(12) United States Patent
Nakamura et al.

(10) Patent No.: US 6,953,847 B2
(45) Date of Patent: Oct. 11, 2005

(54) FAS ANTIGEN DERIVATIVE

(75) Inventors: Norio Nakamura, Tokyo (JP); Shigekazu Nagata, Osaka-fu (JP)

(73) Assignees: Mochida Pharmaceutical Co., Ltd., Tokyo (JP); Osaka Bioscience Institute, Suita (JP)

( * ) Notice: Subject to any disclaimer, the term of this patent is extended or adjusted under 35 U.S.C. 154(b) by 211 days.

(21) Appl. No.: 09/949,713

(22) Filed: Sep. 12, 2001

(65) Prior Publication Data

US 2002/0044944 A1 Apr. 18, 2002

Related U.S. Application Data

(62) Division of application No. 09/180,100, filed as application No. PCT/JP97/01502 on May 1, 1997, now Pat. No. 6,306,395.

(30) Foreign Application Priority Data

May 2, 1996 (JP) ............................................. 8-135760

(51) Int. Cl.[7] ............................................. C07H 21/04
(52) U.S. Cl. ..................... 536/23.5; 536/1; 536/18.7; 536/22.1; 536/23.1; 536/23.4; 530/300; 530/350; 530/385; 530/386; 530/387.1; 435/69.1; 435/320.1; 435/325
(58) Field of Search ................................. 530/300, 350, 530/385, 386, 387.1; 536/1, 18.7, 22.1, 23.1, 23.4, 23.5; 435/320.1, 325, 69.1

(56) References Cited

U.S. PATENT DOCUMENTS 5,116,964 A * 5/1992 Capon et al. ............... 536/23.5
5,874,546 A    2/1999 Nagata et al.

FOREIGN PATENT DOCUMENTS

| EP | 0 675 200 A | 4/1995 |
|----|-------------|--------|
| JP | 5503009 | 5/1993 |
| JP | 0769914 | 3/1995 |
| JP | 7289266 | 11/1995 |
| WO | 9108298 | 6/1991 |
| WO | 9513293 | 5/1995 |

OTHER PUBLICATIONS

Kimura et al. A variant mRNA species encoding a truncated form of fas antigen in the rat liver. Biochemical and Biophysical Research Communication, 198(2): 666–674, Jan. 28, 1994.*

Adachi et al. Aberrant transcription caused by the insertion of an early transposable element in an intron of the Fas antgen gene of lpr mice. Proc. Natl. Sci. USA 90: 1756–1760, Mar. 1993.*

Amino acid database, Alignment between Applicants' Seq Id No: 15 and sequences from Biochem. Biophys. Res. Commun. 1994 and Proc. Natl. Acad. Sci. USA, 1993.*

Tanaka M. et al., "Expression of the functional soluble form of human Fas ligand in activated lymphocytes"; EMBO Journal, vol. 14, No. 6, pp. 1129–1135 (1995).

Tanaka, M. et al., "Fas ligand in human serum", Nature Medicine, vol. 2, pp. 317–322 (1996).

Suda, T. et al., "Purification and Characterization of the Fas–ligand that Induces Apoptosis"; J. Exp. Med.; vol. 179, No. 3, pp. 873–879 (1994).

Itoh et al., Cell, vol. 66 (1991) pp. 233–243.

Tanaka et al., The Empo J., vol 14, No. 6 (1995) pp. 1129–1135.

Suda et al., Cell, vol. 75, (1993) pp. 1169–1178.

Ramsdell et al., Eur. J. Immunol., vol. 24 pp. 928–933, 1994.

Ed. Nikkei Baioteku (Nikkei BP Sha) "Nikkei Baio Saishin–Yogo Jiten '91 (in Japanese" p. 550 (1991).

* cited by examiner

Primary Examiner—Alana M. Harris
(74) Attorney, Agent, or Firm—Birch, Stewart, Kolasch & Birch, LLP

(57) ABSTRACT

This invention provides a novel Fas antigen derivative which comprises at least a part or entire portion of Fas antigen extracellular region polypeptide in which at least one amino acid residue is deleted from a group of amino acid residues starting from the N-terminal amino acid residue of the Fas antigen polypeptide to a cysteine residue most close to the N-terminal side (excluding said cysteine residue), as well as a DNA fragment which encodes said Fas antigen derivative, a recombinant DNA molecule which contains said DNA sequence, a transformant in which said recombinant DNA molecule is introduced, a method for the production of said Fas antigen derivative, a medicament which contains said novel Fas antigen derivative as the active ingredient and a method for the improvement of activities and functions of Fas antigen and the like.

20 Claims, 28 Drawing Sheets

FIG. 1-1

GACGCTTCTGGGGAGTGAGGGAAGCGGTTTACGAGTGACTTC

GCTGGAGCCTCAGGGGCGGGCACTGGCACGGAACACACCCTGAGGCCAGCCCTGGCTGCCCAGGCGGAGCTGCCTC

TTCTCCCGCGGGTTGGTGGACCCGCTCAGTACGGAGTTGGGGAAGCTCTTTCACTTCGGAGGATTGCTCAACAACC

ATG CTG GGC ATC TGG ACC CTC CTA CCT CTG GTT CTT ACG TCT GTT GCT AGA TTA TCG
Met Leu Gly Ile Trp Thr Leu Leu Pro Leu Val Leu Thr Ser Val Ala Arg Leu Ser
                              -10                                    -1  +1

TCC AAA AGT GTT AAT GCC CAA GTG ACT GAC ATC AAC TCC AAG GGA TTG GAA TTG AGG
Ser Lys Ser Val Asn Ala Gln Val Thr Asp Ile Asn Ser Lys Gly Leu Glu Leu Arg
              10                                    20

AAG ACT GTT ACT ACA GTT GAG ACT CAG AAC TTG GAA GGC CTG CAT CAT GAT GGC CAA
Lys Thr Val Thr Thr Val Glu Thr Gln Asn Leu Glu Gly Leu His His Asp Gly Gln
              30                                    40

FIG. 1-2

```
                                        400
TTC TGC CAT AAG CCC TGT CCT CCA GGT GAA AGG AAA GCT AGG GAC TGC ACA GTC AAT
Phe Cys His Lys Pro Cys Pro Pro Gly Glu Arg Lys Ala Arg Asp Cys Thr Val Asn
                                         50                                60
                     450
GGG GAT GAA CCA GAC TGC GTG CCC TGC CAA GAA GGG AAG GAG TAC ACA GAC AAA GCC
Gly Asp Glu Pro Asp Cys Val Pro Cys Gln Glu Gly Lys Glu Tyr Thr Asp Lys Ala
                                70
                     500
CAT TTT TCT TCC AAA TGC AGA AGA TGT AGA TTG TGT GAT GAA GGA CAT GGC TTA GAA
His Phe Ser Ser Lys Cys Arg Arg Cys Arg Leu Cys Asp Glu Gly His Gly Leu Glu
 80                                      90
                    550
GTG GAA ATA AAC TGC ACC CGG ACC CAG AAT ACC AAG TGC AGA TGT AAA CCA AAC TTT
Val Glu Ile Asn Cys Thr Arg Thr Gln Asn Thr Lys Cys Arg Cys Lys Pro Asn Phe
100          *                          110
   600                                                              650
TTT TGT AAC TCT ACT GTA TGT GAA CAC TGT GAC CCT TGC ACC AAA TGT GAA CAT GGA
Phe Cys Asn Ser Thr Val Cys Glu His Cys Asp Pro Cys Thr Lys Cys Glu His Gly
           120                                        130
```

FIG. 1-3

```
                                                                           700
ATC ATC AAG GAA TGC ACA CTC ACC AGC AAC ACC AAG TGC AAA GAG GAA GGA TCC AGA
Ile Ile Lys Glu Cys Thr Leu Thr Ser Asn Thr Lys Cys Lys Glu Glu Gly Ser Arg
        140                                 150
                                                    750
TCT AAC TTG GGG TGG CTT TGT CTT CTT CTT TTG CCA ATT CCA CTA ATT GTT TGG GTG
Ser Asn Leu Gly Trp Leu Cys Leu Leu Leu Leu Pro Ile Pro Leu Ile Val Trp Val
        160                                 170
                                800
AAG AGA AAG GAA CTA CAG AAA ACA TGC AGA AAG CAC AGA AAG GAA AAC CAA GGT TCT
Lys Arg Lys Glu Val Gln Lys Thr Cys Arg Lys His Arg Lys Glu Asn Gln Gly Ser
        180                                 190
                                850
CAT GAA TCT CCA ACC TTA AAT CCT GAA ACA GTG GCA ATA AAT TTA TCT GAT GTT GAC
His Glu Ser Pro Thr Leu Asn Pro Glu Thr Val Ala Ile Asn Leu Ser Asp Val Asp
        200                                 210
                                900
TTG AGT AAA TAT ATC ACC ACT ATT GCT GGA GTC ATG ACA CTA AGT CAA GTT AAA GGC
Leu Ser Lys Tyr Ile Thr Thr Ile Ala Gly Val Met Thr Leu Ser Gln Val Lys Gly
        220                                 230
```

TTT GTT CGA AAG AAT GGT GTC AAT GAA GCC AAA ATA GAT GAG ATC AAG AAT GAC AAT

Phe Val Arg Lys Asn Gly Val Asn Glu Ala Lys Ile Asp Glu Ile Lys Asn Asp Asn 240                                250

1000

GTC CAA GAC ACA GCA GAA CAG AAA GTT CAA CTG CTT CGT AAT TGG CAT CAA CTT

Val Gln Asp Thr Ala Glu Gln Lys Val Gln Leu Leu Arg Asn Trp His Gln Leu

260

1050

CAT GGA AAG AAA GAA GCG TAT GAC ACA TTG ATT AAA GAT CTC AAA AAA

His Gly Lys Lys Glu Ala Tyr Asp Thr Leu Ile Lys Asp Leu Lys Lys 270                             280

FIG. 2-1

```
1100                                               1150
GCC AAT CTT TGT ACT CTT GCA GAG AAA ATT CAG ACT ATC ATC CTC AAG GAC ATT ACT
Ala Asn Leu Cys Thr Leu Ala Glu Lys Ile Gln Thr Ile Ile Leu Lys Asp Ile Thr
            290                                 300
                                                             1200
AGT GAC TCA CAA AAT TCA AAC TTC AGA AAT GAA ATC CAA AGC TTG GTC TAG AGTGAAA
Ser Asp Ser Gln Asn Ser Asn Phe Arg Asn Glu Ile Gln Ser Leu Val End
                            310

1250
AACAACAAATTCAGTTCTGAGTATATGCAATTAGTGTTTGAAAAGATTCTTAATAGCTGGCTGTAAATACTGCTTG 1300                                  1350'
GTTTTTACTGGGTACATTTTATCATTTATTAGCGCTGAAGAGCCAACATATTTGTAGATTTTTAATATCTCATGA

1400
TTCTGCCTCCAACCATGTTTAAAATCTAGTTGGGAAAACAAACTTCATCAAGAGTAAATGCAGTGGCATGCTAAGT 1450                                  1500
ACCCAAATAGGAGTGTATGCAGAGGATGAAAGATTAAGATTATGCTCTGGCATCTAACATATGATTCTGTAGTATG
```

AATGTAATCAGTGTATGTTAGTACAAATGTCTATCCACAGGCTAACCCCACTCTATGAATCAATAGAAGAAGCTAT 1600                                                                1650

GACCTTTTGCTGAAATATCAGTTACTGAACAGGCAGGCCACTTTGCCTCTAAATTACCTCTGATAATTCTAGAGAT

1700

TTTACCATATTTCTAAACTTTGTTTATAACTCTGAGAAGATCATATTTATGTAAAGTATATGTATTTGAGTGCAGA 1750                                                                1800

ATTTAAATAAGGCTCTACCTCAAAGACCTTTGCACAGTTTATTGGTGTCATATTATACAATATTTCAATTGTGAAT

1850

TCACATAGAAAACATTAAATTATAATGTTTGACTATTATATATGTCTATGCATTTTACTGGCTCAAAACTACCTAC 1900                                                                1950

TTCTTCTCAGGCATCAAAAGCATTTTGAGCAGGAGAGTATTACTAGAGCTTTGCCACCTCTCCATTTTTGCCTTG

GTGCTCATCTTAATGGCCTAATGCACCCCCAAACATGGAAATATCACCAAAAAATACTTAATAGTCCACCAAAAGG 2050                                       2100

CAAGACTGCCCTTAGAAATTCTAGCCTGGTTTGGAGATACTAACTGCTCTCAGAGAAAGTAGCTTTGTGACATGTC

2150

ATGAACCCATGTTTGCAATCAAAGATGATAAAATAGATTCTTATTTTTCCCCCACCCCCGAAAATGTTCAATAATG 2200                         2250

TCCCATGTAAAACCTGCTACAAATGGCAGCTTATACATAGCAATGGTAAAATCATCATCTGGATTTAGGAATTG

2300

CTCTTGTCATACCCTCAAGTTTCTAAGATTTAAGATTCTCCTTACTACTATCCTACGTTTAAATATCTTTGAAAGT 2350                                       2400

TTGTATTAAATGTGAATTTTAAGAAATAATATTTATATTTCTGTAAATGTAAACTGTGAAGATAGTTATAAACT

GAAGCAGATACCTGGAACCACCTAAAGAACTTCCATTTATGGAGGATTTTTTTGCCCCTTGTGTTTGGAATTATAA

2500

AATATAGGTAAAAGTACGTAATTAAATAATGTTTTTG

FIG. 3-1 tttcttccatttcaggtgtcgtgaggaattcacc

```
                         50
ATG CTG GGC ATC TGG ACC CTC CTA CCT CTG
Met Leu Gly Ile Trp Thr Leu Leu Pro Leu
                                    -10
   hFas antigen signal peptide
GTT CTG ACT AGT GTC GCT  ACT CAG AAC TTG
Val Leu Thr Ser Val Ala  Thr Gln Asn Leu
                     -1   1
   100                   └→ hFas(nd29)
GAA GGC CTG CAT CAT GAT GGC CAA TTC TGC
Glu Gly Leu His His Asp Gly Gln Phe Cys
                        10
                                150
CAT AAG CCC TGT CCT CCA GGT GAA AGG AAA
His Lys Pro Cys Pro Pro Gly Glu Arg Lys GCT AGG GAC TGC ACA GTC AAT GGG GAT GAA
Ala Arg Asp Cys Thr Val Asn Gly Asp Glu 200
CCA GAC TGC GTG CCC TGC CAA GAA GGG AAG
Pro Asp Cys Val Pro Cys Gln Glu Gly Lys GAG TAC ACA GAC AAA GCC CAT TTT TCT TCC
Glu Tyr Thr Asp Lys Ala His Phe Ser Ser
                        50
   250
AAA TGC AGA AGA TGT AGA TTG TGT GAT GAA
Lys Cys Arg Arg Cys Arg Leu Cys Asp Glu
```

FIG. 3-2

```
                                                    300
GGA CAT GGC TTA GAA GTG GAA ATA AAC TGC
Gly His Gly Leu Glu Val Glu Ile Asn Cys
                                         *

ACC CGG ACC CAG AAT ACC AAG TGC AGA TGT
Thr Arg Thr Gln Asn Thr Lys Cys Arg Cys

350
AAA CCA AAC TTT TTT TGT AAC TCT ACT GTA
Lys Pro Asn Phe Phe Cys Asn Ser Thr Val
                             *

TGT GAA CAC TGT GAC CCT TGC ACC AAA TGT
Cys Glu His Cys Asp Pro Cys Thr Lys Cys
                            100
    400
GAA CAT GGA ATC ATC AAG GAA TGC ACA CTC
Glu His Gly Ile Ile Lys Glu Cys Thr Leu

450
ACC AGC AAC ACC AAG TGC AAA GAG GAA GGA
Thr Ser Asn Thr Lys Cys Lys Glu Glu Gly

TCC AGA TCT AAC TAA TAG    ggtaccttctgag
Ser Arg Ser Asn *** ***
```

FIG. 4-1 ttttcttccatttcaggtgtcgtgaggaattcacc
50

| ATG | CTG | GGC | ATC | TGG | ACC | CTC | CTA | CCT | CTG |
|-----|-----|-----|-----|-----|-----|-----|-----|-----|-----|
| Met | Leu | Gly | Ile | Trp | Thr | Leu | Leu | Pro | Leu |

−10 hFas antigen signal peptide

| GTT | CTG | ACT | AGT | GTC | GCT | ACT | CAG | AAC | TTG |
|-----|-----|-----|-----|-----|-----|-----|-----|-----|-----|
| Val | Leu | Thr | Ser | Val | Ala | Thr | Gln | Asn | Leu |

−1　1
→hFas(nd29)

100

| GAA | GGC | CTG | CAT | CAT | GAT | GGC | CAA | TTC | TGC |
|-----|-----|-----|-----|-----|-----|-----|-----|-----|-----|
| Glu | Gly | Leu | His | His | Asp | Gly | Gln | Phe | Cys |

150

| CAT | AAG | CCC | TGT | CCT | CCA | GGT | GAA | AGG | AAA |
|-----|-----|-----|-----|-----|-----|-----|-----|-----|-----|
| His | Lys | Pro | Cys | Pro | Pro | Gly | Glu | Arg | Lys |

| GCT | AGG | GAC | TGC | ACA | GTC | AAT | GGG | GAT | GAA |
|-----|-----|-----|-----|-----|-----|-----|-----|-----|-----|
| Ala | Arg | Asp | Cys | Thr | Val | Asn | Gly | Asp | Glu |

200

| CCA | GAC | TGC | GTG | CCC | TGC | CAA | GAA | GGG | AAG |
|-----|-----|-----|-----|-----|-----|-----|-----|-----|-----|
| Pro | Asp | Cys | Val | Pro | Cys | Gln | Glu | Gly | Lys |

| GAG | TAC | ACA | GAC | AAA | GCC | CAT | TTT | TCT | TCC |
|-----|-----|-----|-----|-----|-----|-----|-----|-----|-----|
| Glu | Tyr | Thr | Asp | Lys | Ala | His | Phe | Ser | Ser |

50

250

| AAA | TGC | AGA | AGA | TGT | AGA | TTG | TGT | GAT | GAA |
|-----|-----|-----|-----|-----|-----|-----|-----|-----|-----|
| Lys | Cys | Arg | Arg | Cys | Arg | Leu | Cys | Asp | Glu |

FIG. 4-2

```
                                                        300
GGA CAT GGC TTA GAA GTG GAA ATA AAC TGC
Gly His Gly Leu Glu Val Glu Ile Asn Cys
                                         *

ACC CGG ACC CAG AAT ACC AAG TGC AGA TGT
Thr Arg Thr Gln Asn Thr Lys Cys Arg Cys

350
AAA CCA AAC TTT TTT TGT AAC TCT ACT GTA
Lys Pro Asn Phe Phe Cys Asn Ser Thr Val
                            *

TGT GAA CAC TGT GAC CCT TGC ACC AAA TGT
Cys Glu His Cys Asp Pro Cys Thr Lys Cys
                        100
    400
GAA CAT GGA ATC ATC AAG GAA TGC ACA CTC
Glu His Gly Ile Ile Lys Glu Cys Thr Leu

450
ACC AGC AAC ACC AAG TGC AAA GAG GAA GGA
Thr Ser Asn Thr Lys Cys Lys Glu Glu Gly

TCC AGA TCT AAC GAG CCC AAA TCT TGT GAC
Ser Arg Ser Asn Glu Pro Lys Ser Cys Asp
                     └──→ hIgG1 Fc
                    500
AAA ACT CAC ACA TGC CCA CCG TGC CCA GCA
Lys Thr His Thr Cys Pro Pro Cys Pro Ala
```

FIG. 4-3

```
CCT GAA CTC CTG GGG GGA CCG TCA GTC TTC
Pro Glu Leu Leu Gly Gly Pro Ser Val Phe
                        150
    550
CTC TTC CCC CCA AAA CCC AAG GAC ACC CTC
Leu Phe Pro Pro Lys Pro Lys Asp Thr Leu
                                    600
ATG ATC TCC CGG ACC CCT GAG GTC ACA TGC
Met Ile Ser Arg Thr Pro Glu Val Thr Cys

GTG GTG GTG GAC GTG AGC CAC GAA GAC CCT
Val Val Val Asp Val Ser His Glu Asp Pro
                650
GAG GTC AAG TTC AAC TGG TAC GTG GAC GGC
Glu Val Lys Phe Asn Trp Tyr Val Asp Gly

GTG GAG GTG CAT AAT GCC AAG ACA AAG CCG
Val Glu Val His Asn Ala Lys Thr Lys Pro
                        200
    700
CGG GAG GAG CAG TAC AAC AGC ACG TAC CGT
Arg Glu Glu Gln Tyr Asn Ser Thr Tyr Arg
                                    750
GTG GTC AGC GTC CTC ACC GTC CTG CAC CAG
Val Val Ser Val Leu Thr Val Leu His Gln
```

FIG. 4-4

```
GAC TGG CTG AAT GGC AAG GAG TAC AAG TGC
Asp Trp Leu Asn Gly Lys Glu Tyr Lys Cys

800
AAG GTC TCC AAC AAA GCC CTC CCA GCC CCC
Lys Val Ser Asn Lys Ala Leu Pro Ala Pro

ATC GAG AAA ACC ATC TCC AAA GCC AAA GGG
Ile Glu Lys Thr Ile Ser Lys Ala Lys Gly
                    250
 850
CAG CCC CGA GAA CCA CAG GTG TAC ACC CTG
Gln Pro Arg Glu Pro Gln Val Tyr Thr Leu

900
CCC CCA TCC CGG GAT GAG CTG ACC AAG AAC
Pro Pro Ser Arg Asp Glu Leu Thr Lys Asn

CAG GTC AGC CTG ACC TGC CTG GTC AAA GGC
Gln Val Ser Leu Thr Cys Leu Val Lys Gly

950
TTC TAT CCC AGC GAC ATC GCC GTG GAG TGG
Phe Tyr Pro Ser Asp Ile Ala Val Glu Trp

GAG AGC AAT GGG CAG CCG GAG AAC AAC TAC
Glu Ser Asn Gly Gln Pro Glu Asn Asn Tyr
                    300
```

FIG. 4-5

```
1000
AAG ACC ACG CCT CCC GTG CTG GAC TCC GAC
Lys Thr Thr Pro Pro Val Leu Asp Ser Asp

1050
GGC TCC TTC TTC CTC TAC AGC AAG CTC ACC
Gly Ser Phe Phe Leu Tyr Ser Lys Leu Thr

GTG GAC AAG AGC AGG TGG CAG CAG GGG AAC
Val Asp Lys Ser Arg Trp Gln Gln Gly Asn

1100
GTC TTC TCA TGC TCC GTG ATG CAT GAG GCT
Val Phe Ser Cys Ser Val Met His Glu Ala

CTG CAC AAC CAC TAC ACG CAG AAG AGC CTC
Leu His Asn His Tyr Thr Gln Lys Ser Leu
                        350
  1150
TCC CTG TCT CCG GGT AAA TGA TAG    ggtacc
Ser Leu Ser Pro Gly Lys * * ttctgag
```

FIG. 5-1 ttttcttccatttcaggtgtcgtgaggaattcacc

50

| ATG | CTG | GGC | ATC | TGG | ACC | CTC | CTA | CCT | CTG |
|-----|-----|-----|-----|-----|-----|-----|-----|-----|-----|
| Met | Leu | Gly | Ile | Trp | Thr | Leu | Leu | Pro | Leu |

−10 hFas antigen signal peptide

| GTT | CTG | ACT | AGT | GTC | GCT | ACT | CAG | AAC | TTG |
|-----|-----|-----|-----|-----|-----|-----|-----|-----|-----|
| Val | Leu | Thr | Ser | Val | Ala | Thr | Gln | Asn | Leu |

−1 | 1
→ hFas(nd29)

100

| GAA | GGC | CTG | CAT | CAT | GAT | GGC | CAA | TTC | TGC |
|-----|-----|-----|-----|-----|-----|-----|-----|-----|-----|
| Glu | Gly | Leu | His | His | Asp | Gly | Gln | Phe | Cys |

150

| CAT | AAG | CCC | TGT | CCT | CCA | GGT | GAA | AGG | AAA |
|-----|-----|-----|-----|-----|-----|-----|-----|-----|-----|
| His | Lys | Pro | Cys | Pro | Pro | Gly | Glu | Arg | Lys |

| GCT | AGG | GAC | TGC | ACA | GTC | AAT | GGG | GAT | GAA |
|-----|-----|-----|-----|-----|-----|-----|-----|-----|-----|
| Ala | Arg | Asp | Cys | Thr | Val | Asn | Gly | Asp | Glu |

200

| CCA | GAC | TGC | GTG | CCC | TGC | CAA | GAA | GGG | AAG |
|-----|-----|-----|-----|-----|-----|-----|-----|-----|-----|
| Pro | Asp | Cys | Val | Pro | Cys | Gln | Glu | Gly | Lys |

| GAG | TAC | ACA | GAC | AAA | GCC | CAT | TTT | TCT | TCC |
|-----|-----|-----|-----|-----|-----|-----|-----|-----|-----|
| Glu | Tyr | Thr | Asp | Lys | Ala | His | Phe | Ser | Ser |

50

250

| AAA | TGC | AGA | AGA | TGT | AGA | TTG | TGT | GAT | GAA |
|-----|-----|-----|-----|-----|-----|-----|-----|-----|-----|
| Lys | Cys | Arg | Arg | Cys | Arg | Leu | Cys | Asp | Glu |

FIG. 5-2

```
                                          300
GGA CAT GGC TTA GAA GTG GAA ATA AAC TGC
Gly His Gly Leu Glu Val Glu Ile Asn Cys
                                     *

ACC CGG ACC CAG AAT ACC AAG TGC AGA TGT
Thr Arg Thr Gln Asn Thr Lys Cys Arg Cys

350
AAA CCA AAC TTT TTT TGT AAC TCT ACT GTA
Lys Pro Asn Phe Phe Cys Asn Ser Thr Val
                         *

TGT GAA CAC TGT GAC CCT TGC ACC AAA TGT
Cys Glu His Cys Asp Pro Cys Thr Lys Cys
                        100
   400
GAA CAT GGA ATC ATC AAG GAA TGC ACA CTC
Glu His Gly Ile Ile Lys Glu Cys Thr Leu

450
ACC AGC AAC ACC AAG TGC AAA GAG GAA GGA
Thr Ser Asn Thr Lys Cys Lys Glu Glu Gly

TCC AGA TCT AAC GAG CCC AAA TCT TGT GAC
Ser Arg Ser Asn Glu Pro Lys Ser Cys Asp
                       └──► hIgG1 hinge
              500
AAA ACT CAC ACA TGC CCA CCG TGC CCA TAG
Lys Thr His Thr Cys Pro Pro Cys Pro ***
```

FIG. 5-3

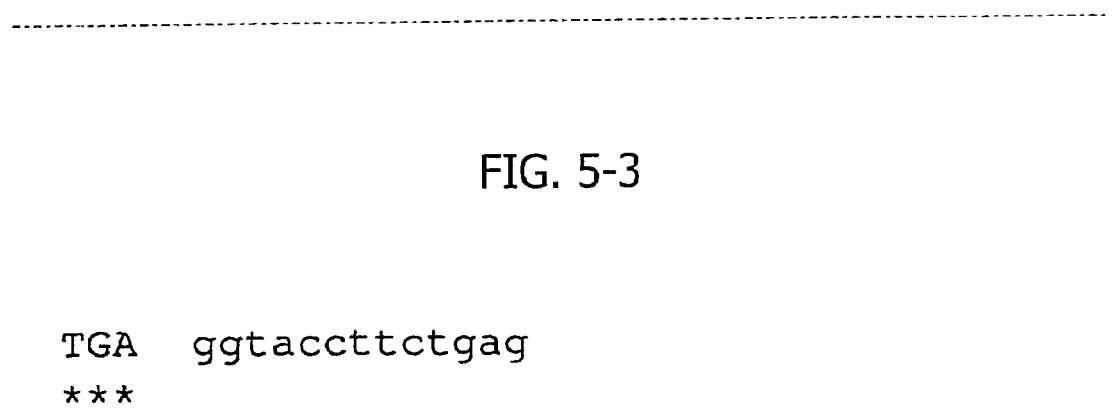

```
TGA   ggtaccttctgag
***
```

(Non-reducing condition)
Lane 1～3 : shFas(nd29)-Fc
Lane 4 : hFas-Fc (Reducing condition)
Lane 5～7 : shFas(nd29)-Fc
Lane 8 : hFas-Fc Lane 1: non-reducing condition
Lane 2: reducing condition (Non-reducing condition)
Lane 1 : sample befor gel filtration separation
Lane 2 : fraction 1
Lane 3 : fraction 2
Lane 4 : fraction 3
Lane 5 : fraction 4

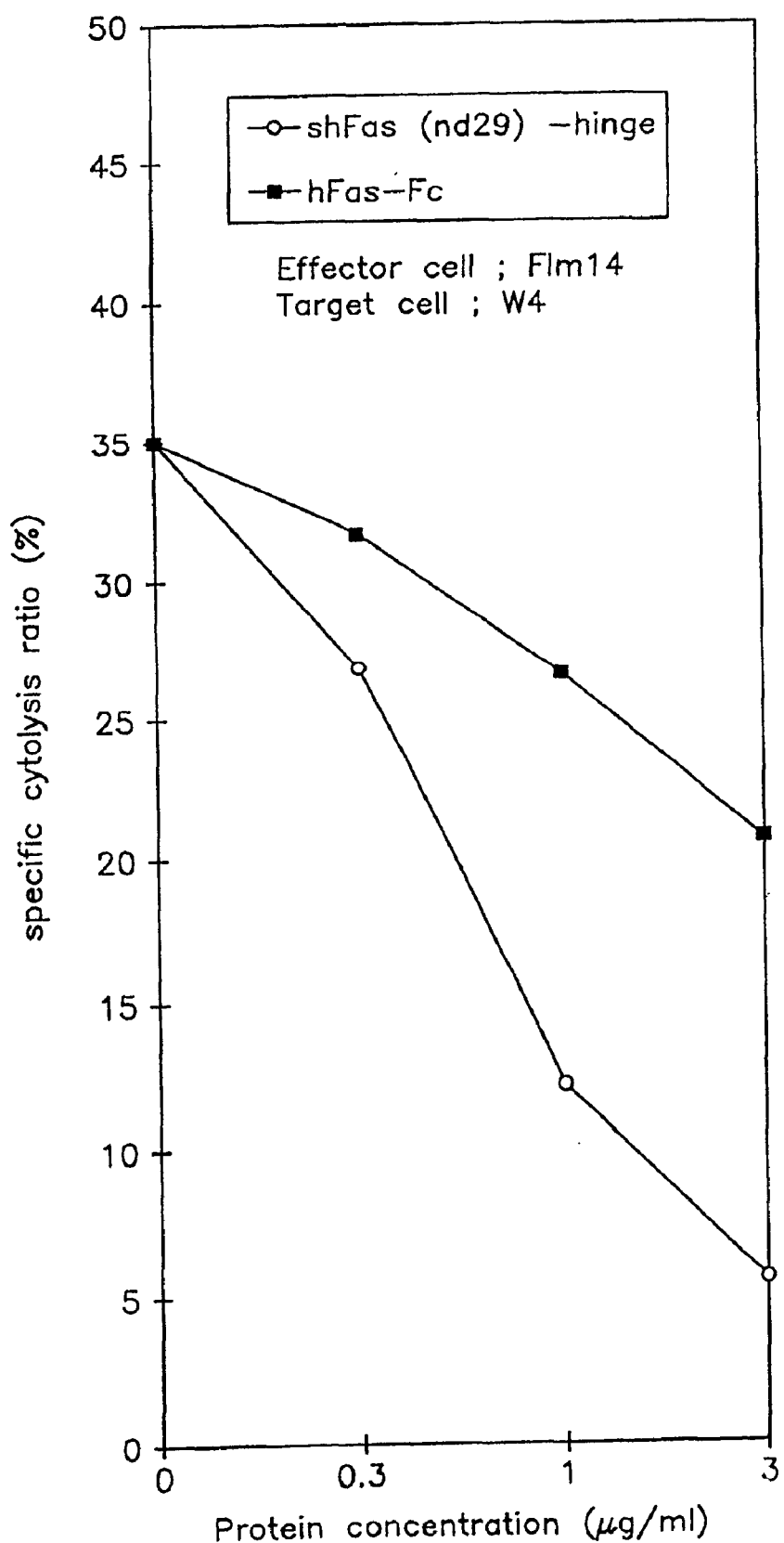

GOT and GPT after 8 hours (average±standard deviation)

GOT and GPT after 24 hours (average±standard deviation)

GOT and GPT after 8 hours (average±standard deviation)

GOT and GPT after 24 hours (average±standard deviation)

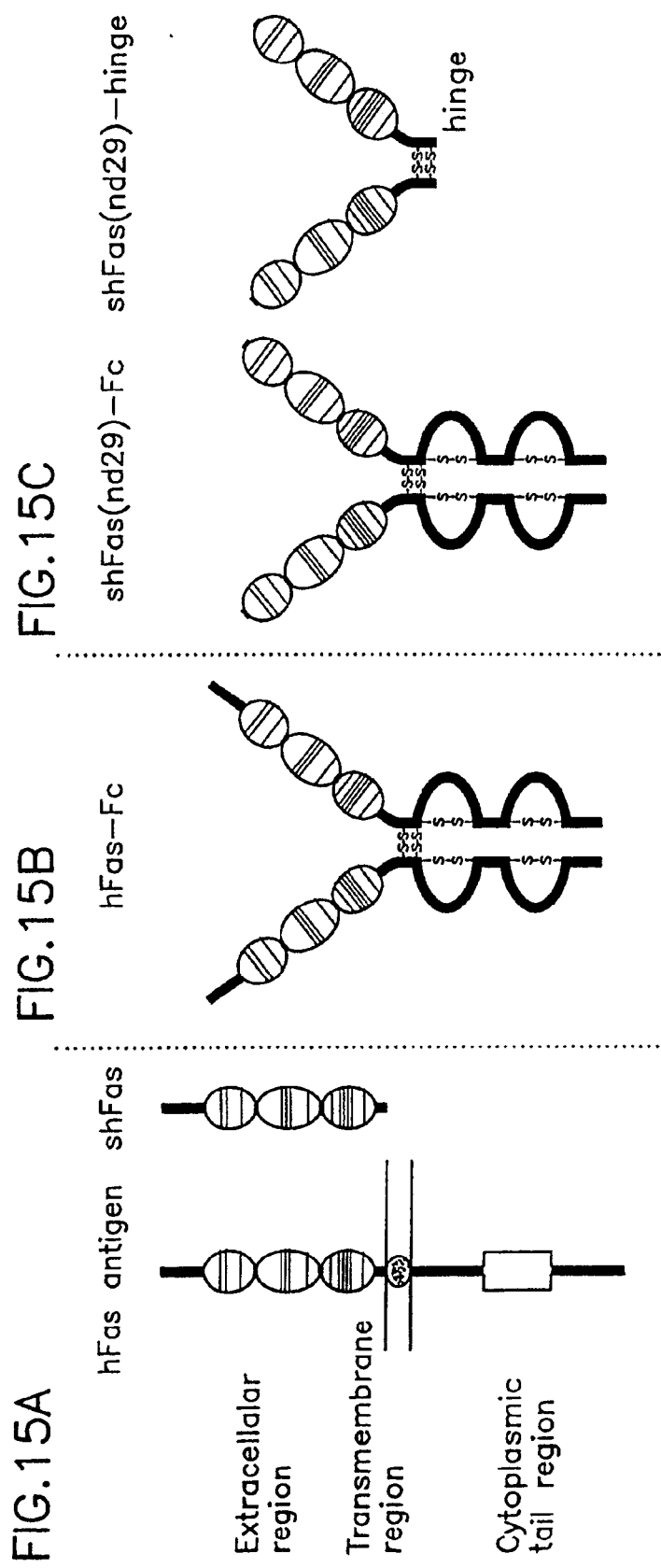

SEQUENCE LISTING

```
<160> NUMBER OF SEQ ID NOS: 25

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Sense
      Primer 1

<400> SEQUENCE: 1
ctgactagtg tcgctactca gaacttggaa                                       30

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: Antisense
      Primer 2

<400> SEQUENCE: 2
gtcaagcttg gtaccctatt agttagatct ggatccttc                             39

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Sense
      Primer 3

<400> SEQUENCE: 3
tcacaagccc agcaacacca ag                                               22

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Antisense
      Primer 4

<400> SEQUENCE: 4
gcttgccggc cgtcgcactc                                                  20

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Sense
      Primer 5

<400> SEQUENCE: 5
gaaggatcca gatctaacga gcccaaatct tgt                                   33
```

```
<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Antisense
      Primer 6

<400> SEQUENCE: 6
gtcggtaccc tatcatttac ccggagacag                                           30

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Sense
      Primer 7

<400> SEQUENCE: 7
tgcgaattca ccatgctggg catctgg                                              27

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Antisense
      Primer 8

<400> SEQUENCE: 8
cggggtacct cactatgggc acggtgggca                                           30

<210> SEQ ID NO 9
<211> LENGTH: 128
<212> TYPE: PRT
<213> ORGANISM: Homo sapiens

<400> SEQUENCE: 9

Thr Gln Asn Leu Glu Gly Leu His His Asp Gly Gln Phe Cys His Lys
 1               5                  10                  15

Pro Cys Pro Pro Gly Glu Arg Lys Ala Arg Asp Cys Thr Val Asn Gly
                20                  25                  30

Asp Glu Pro Asp Cys Val Pro Cys Gln Glu Gly Lys Glu Tyr Thr Asp
            35                  40                  45

Lys Ala His Phe Ser Ser Lys Cys Arg Arg Cys Arg Leu Cys Asp Glu
        50                  55                  60

Gly His Gly Leu Glu Val Glu Ile Asn Cys Thr Arg Thr Gln Asn Thr
    65                  70                  75                  80

Lys Cys Arg Cys Lys Pro Asn Phe Phe Cys Asn Ser Thr Val Cys Glu
                85                  90                  95

His Cys Asp Pro Cys Thr Lys Cys Glu His Gly Ile Ile Lys Glu Cys
            100                 105                 110

Thr Leu Thr Ser Asn Thr Lys Cys Lys Glu Glu Gly Ser Arg Ser Asn
        115                 120                 125

<210> SEQ ID NO 10
<211> LENGTH: 143
<212> TYPE: PRT
<213> ORGANISM: Homo sapiens

<400> SEQUENCE: 10
```

-continued

```
Thr Gln Asn Leu Glu Gly Leu His His Asp Gly Gln Phe Cys His Lys
 1               5                  10                  15

Pro Cys Pro Pro Gly Glu Arg Lys Ala Arg Asp Cys Thr Val Asn Gly
                20                  25                  30

Asp Glu Pro Asp Cys Val Pro Cys Gln Glu Gly Lys Glu Tyr Thr Asp
            35                  40                  45

Lys Ala His Phe Ser Ser Lys Cys Arg Arg Cys Arg Leu Cys Asp Glu
        50                  55                  60

Gly His Gly Leu Glu Val Glu Ile Asn Cys Thr Arg Thr Gln Asn Thr
65                  70                  75                  80

Lys Cys Arg Cys Lys Pro Asn Phe Phe Cys Asn Ser Thr Val Cys Glu
                85                  90                  95

His Cys Asp Pro Cys Thr Lys Cys Glu His Gly Ile Ile Lys Glu Cys
            100                 105                 110

Thr Leu Thr Ser Asn Thr Lys Cys Lys Glu Glu Gly Ser Arg Ser Asn
        115                 120                 125

Glu Pro Lys Ser Cys Asp Lys Thr His Thr Cys Pro Pro Cys Pro
    130                 135                 140
```

<210> SEQ ID NO 11
<211> LENGTH: 360
<212> TYPE: PRT
<213> ORGANISM: Homo sapiens

<400> SEQUENCE: 11

```
Thr Gln Asn Leu Glu Gly Leu His His Asp Gly Gln Phe Cys His Lys
 1               5                  10                  15

Pro Cys Pro Pro Gly Glu Arg Lys Ala Arg Asp Cys Thr Val Asn Gly
                20                  25                  30

Asp Glu Pro Asp Cys Val Pro Cys Gln Glu Gly Lys Glu Tyr Thr Asp
            35                  40                  45

Lys Ala His Phe Ser Ser Lys Cys Arg Arg Cys Arg Leu Cys Asp Glu
        50                  55                  60

Gly His Gly Leu Glu Val Glu Ile Asn Cys Thr Arg Thr Gln Asn Thr
65                  70                  75                  80

Lys Cys Arg Cys Lys Pro Asn Phe Phe Cys Asn Ser Thr Val Cys Glu
                85                  90                  95

His Cys Asp Pro Cys Thr Lys Cys Glu His Gly Ile Ile Lys Glu Cys
            100                 105                 110

Thr Leu Thr Ser Asn Thr Lys Cys Lys Glu Glu Gly Ser Arg Ser Asn
        115                 120                 125

Glu Pro Lys Ser Cys Asp Lys Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240
```

```
Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Asp Glu Leu Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 12
<211> LENGTH: 384
<212> TYPE: DNA
<213> ORGANISM: Homo sapiens

<400> SEQUENCE: 12
actcagaact tggaaggcct gcatcatgat ggccaattct gccataagcc ctgtcctcca      60
ggtgaaagga aagctaggga ctgcacagtc aatggggatg aaccagactg cgtgccctgc     120
caagaaggga aggagtacac agacaaagcc cattttttctt ccaaatgcag aagatgtaga    180
ttgtgtgatg aaggacatgg cttagaagtg gaaataaact gcacccggac ccagaatacc    240
aagtgcagat gtaaaccaaa ctttttttgt aactctactg tatgtgaaca ctgtgaccct    300
tgcaccaaat gtgaacatgg aatcatcaag gaatgcacac tcaccagcaa caccaagtgc    360
aaagaggaag gatccagatc taac                                            384

<210> SEQ ID NO 13
<211> LENGTH: 429
<212> TYPE: DNA
<213> ORGANISM: Homo sapiens

<400> SEQUENCE: 13
actcagaact tggaaggcct gcatcatgat ggccaattct gccataagcc ctgtcctcca      60
ggtgaaagga aagctaggga ctgcacagtc aatggggatg aaccagactg cgtgccctgc     120
caagaaggga aggagtacac agacaaagcc cattttttctt ccaaatgcag aagatgtaga    180
ttgtgtgatg aaggacatgg cttagaagtg gaaataaact gcacccggac ccagaatacc    240
aagtgcagat gtaaaccaaa ctttttttgt aactctactg tatgtgaaca ctgtgaccct    300
tgcaccaaat gtgaacatgg aatcatcaag gaatgcacac tcaccagcaa caccaagtgc    360
aaagaggaag gatccagatc taacgagccc aaatcttgtg acaaaactca cacatgccca    420
ccgtgccca                                                             429

<210> SEQ ID NO 14
<211> LENGTH: 1080
<212> TYPE: DNA
<213> ORGANISM: Homo sapiens

<400> SEQUENCE: 14
```

-continued

```
actcagaact tggaaggcct gcatcatgat ggccaattct gccataagcc ctgtcctcca        60
ggtgaaagga aagctaggga ctgcacagtc aatggggatg aaccagactg cgtgccctgc       120
caagaaggga aggagtacac agacaaagcc cattttttctt ccaaatgcag aagatgtaga      180
ttgtgtgatg aaggacatgg cttagaagtg gaaataaact gcacccggac ccagaatacc      240
aagtgcagat gtaaaccaaa cttttttttgt aactctactg tatgtgaaca ctgtgaccct     300
tgcaccaaat gtgaacatgg aatcatcaag gaatgcacac tcaccagcaa caccaagtgc      360
aaagaggaag gatccagatc taacgagccc aaatcttgtg acaaaactca cacatgccca      420
ccgtgcccag cacctgaact cctgggggga ccgtcagtct tcctcttccc cccaaaaccc      480
aaggacaccc tcatgatctc ccggacccct gaggtcacat gcgtggtggt ggacgtgagc      540
cacgaagacc ctgaggtcaa gttcaactgg tacgtggacg gcgtggaggt gcataatgcc      600
aagacaaagc cgcgggagga gcagtacaac agcacgtacc gtgtggtcag cgtcctcacc      660
gtcctgcacc aggactggct gaatggcaag gagtacaagt gcaaggtctc caacaaagcc      720
ctcccagccc ccatcgagaa aaccatctcc aaagccaaag gcagccccg agaaccacag       780 gtgtacaccc tgcccccatc ccgggatgag ctgaccaaga accaggtcag cctgacctgc      840
ctggtcaaag gcttctatcc cagcgacatc gccgtggagt gggagagcaa tgggcagccg      900
gagaacaact acaagaccac gcctcccgtg ctggactccg acggctcctt cttcctctac      960
agcaagctca ccgtggacaa gagcaggtgg cagcagggga acgtcttctc atgctccgtg     1020
atgcatgagg ctctgcacaa ccactacacg cagaagagcc tctccctgtc tccgggtaaa     1080
```

<210> SEQ ID NO 15
<211> LENGTH: 157
<212> TYPE: PRT
<213> ORGANISM: Homo sapiens

<400> SEQUENCE: 15

```
Arg Leu Ser Ser Lys Ser Val Asn Ala Gln Val Thr Asp Ile Asn Ser
  1               5                  10                  15

Lys Gly Leu Glu Leu Arg Lys Thr Val Thr Val Glu Thr Gln Asn
             20                  25                  30

Leu Glu Gly Leu His His Asp Gly Gln Phe Cys His Lys Pro Cys Pro
         35                  40                  45

Pro Gly Glu Arg Lys Ala Arg Asp Cys Thr Val Asn Gly Asp Glu Pro
     50                  55                  60

Asp Cys Val Pro Cys Gln Glu Gly Lys Glu Tyr Thr Asp Lys Ala His
 65                  70                  75                  80

Phe Ser Ser Lys Cys Arg Arg Cys Arg Leu Cys Asp Glu Gly His Gly
                 85                  90                  95

Leu Glu Val Glu Ile Asn Cys Thr Arg Thr Gln Asn Thr Lys Cys Arg
            100                 105                 110

Cys Lys Pro Asn Phe Phe Cys Asn Ser Thr Val Cys Glu His Cys Asp
        115                 120                 125

Pro Cys Thr Lys Cys Glu His Gly Ile Ile Lys Glu Cys Thr Leu Thr
    130                 135                 140

Ser Asn Thr Lys Cys Lys Glu Glu Gly Ser Arg Ser Asn
145                 150                 155
```

<210> SEQ ID NO 16
<211> LENGTH: 2534
<212> TYPE: DNA

<213> ORGANISM: Homo sapiens

<400> SEQUENCE: 16

| | | | | | |
|---|---|---|---|---|---|
| gacgcttctg | gggagtgagg | gaagcggttt | acgagtgact | tggctggagc | ctcaggggcg | 60 |
| ggcactggca | cggaacacac | cctgaggcca | gccctggctg | cccaggcgga | gctgcctctt | 120 |
| ctcccgcggg | ttggtggacc | cgctcagtac | ggagttgggg | aagctctttc | acttcggagg | 180 |
| attgctcaac | aaccatgctg | ggcatctgga | ccctcctacc | tctggttctt | acgtctgttg | 240 |
| ctagattatc | gtccaaaagt | gttaatgccc | aagtgactga | catcaactcc | aagggattgg | 300 |
| aattgaggaa | gactgttact | acagttgaga | ctcagaactt | ggaaggcctg | catcatgatg | 360 |
| gccaattctg | ccataagccc | tgtcctccag | gtgaaaggaa | agctagggac | tgcacagtca | 420 |
| atggggatga | accagactgc | gtgccctgcc | aagaagggaa | ggagtacaca | gacaaagccc | 480 |
| attttcttc | caaatgcaga | agatgtagat | tgtgtgatga | aggacatggc | ttagaagtgg | 540 |
| aaataaactg | cacccggacc | cagaatacca | agtgcagatg | taaaccaaac | ttttttgta | 600 |
| actctactgt | atgtgaacac | tgtgacccct | gcaccaaatg | tgaacatgga | atcatcaagg | 660 |
| aatgcacact | caccagcaac | accaagtgca | agaggaagg | atccagatct | aacttggggt | 720 |
| ggctttgtct | tcttcttttg | ccaattccac | taattgtttg | ggtgaagaga | aggaagtac | 780 |
| agaaaacatg | cagaaagcac | agaaaggaaa | accaaggttc | tcatgaatct | ccaaccttaa | 840 |
| atcctgaaac | agtggcaata | aatttatctg | atgttgactt | gagtaaatat | atcaccacta | 900 |
| ttgctggagt | catgacacta | agtcaagtta | aaggctttgt | tcgaaagaat | ggtgtcaatg | 960 |
| aagccaaaat | agatgagatc | aagaatgaca | atgtccaaga | cacagcagaa | cagaaagttc | 1020 |
| aactgcttcg | taattggcat | caacttcatg | gaaagaaaga | agcgtatgac | acattgatta | 1080 |
| aagatctcaa | aaaagccaat | ctttgtactc | ttgcagagaa | aattcagact | atcatcctca | 1140 |
| aggacattac | tagtgactca | gaaaattcaa | acttcagaaa | tgaaatccaa | agcttggtct | 1200 |
| agagtgaaaa | acaacaaatt | cagttctgag | tatatgcaat | tagtgtttga | aaagattctt | 1260 |
| aatagctggc | tgtaaatact | gcttggtttt | ttactgggta | cattttatca | tttattagcg | 1320 |
| ctgaagagcc | aacatatttg | tagatttta | atatctcatg | attctgcctc | caaggatgtt | 1380 |
| taaaatctag | ttgggaaaac | aaacttcatc | aagagtaaat | gcagtggcat | gctaagtacc | 1440 |
| caaataggag | tgtatgcaga | ggatgaaaga | ttaagattat | gctctggcat | ctaacatatg | 1500 |
| attctgtagt | atgaatgtaa | tcagtgtatg | ttagtacaaa | tgtctatcca | caggctaacc | 1560 |
| ccactctatg | aatcaataga | agaagctatg | acctttgct | gaaatatcag | ttactgaaca | 1620 |
| ggcaggccac | tttgcctcta | aattacctct | gataattcta | gagattttac | catatttcta | 1680 |
| aactttgttt | ataactctga | gaagatcata | tttatgtaaa | gtatatgtat | ttgagtgcag | 1740 |
| aatttaaata | aggctctacc | tcaaagacct | ttgcacagtt | tattggtgtc | atattataca | 1800 |
| atatttcaat | tgtgaattca | catagaaaac | attaaattat | aatgtttgac | tattatatat | 1860 |
| gtgtatgcat | tttactggct | caaaactacc | tacttctttc | tcaggcatca | aaagcatttt | 1920 |
| gagcaggaga | gtattactag | agctttgcca | cctctccatt | tttgccttgg | tgctcatctt | 1980 |
| aatggcctaa | tgcaccccca | aacatggaaa | tatcaccaaa | aaatacttaa | tagtccacca | 2040 |
| aaaggcaaga | ctgcccttag | aaattctagc | ctggtttgga | gatactaact | gctctcagag | 2100 |
| aaagtagctt | tgtgacatgt | catgaaccca | tgtttgcaat | caaagatgat | aaaatagatt | 2160 |
| cttatttttc | ccccaccccc | gaaatgttc | aataatgtcc | catgtaaaac | ctgctacaaa | 2220 |
| tggcagctta | tacatagcaa | tggtaaaatc | atcatctgga | tttaggaatt | gctcttgtca | 2280 |

```
taccctcaag tttctaagat ttaagattct ccttactact atcctacgtt taaatatctt    2340
tgaaagtttg tattaaatgt gaatttttaag aaataatatt tatatttctg taaatgtaaa    2400
ctgtgaagat agttataaac tgaagcagat acctggaacc acctaaagaa cttccattta    2460
tggaggattt ttttgcccct tgtgtttgga attataaaat ataggtaaaa gtacgtaatt    2520
aaataatgtt tttg                                                      2534
```

<210> SEQ ID NO 17
<211> LENGTH: 486
<212> TYPE: DNA
<213> ORGANISM: Homo sapiens

<400> SEQUENCE: 17

```
ttttcttcca tttcaggtgt cgtgaggaat tcaccatgct gggcatctgg accctcctac      60
ctctggttct gactagtgtc gctactcaga acttggaagg cctgcatcat gatggccaat     120
tctgccataa gccctgtcct ccaggtgaaa ggaaagctag ggactgcaca gtcaatgggg     180
atgaaccaga ctgcgtgccc tgccaagaag ggaaggagta cacagacaaa gcccattttt     240
cttccaaatg cagaagatgt agattgtgtg atgaaggaca tggcttagaa gtggaaataa     300
actgcacccg gacccagaat accaagtgca gatgtaaacc aaactttttt tgtaactcta     360
ctgtatgtga acactgtgac ccttgcacca aatgtgaaca tggaatcatc aaggaatgca     420
cactcaccag caacaccaag tgcaaagagg aaggatccag atctaactaa tagggtacct     480
tctgag                                                                486
```

<210> SEQ ID NO 18
<211> LENGTH: 1182
<212> TYPE: DNA
<213> ORGANISM: Homo sapiens

<400> SEQUENCE: 18

```
ttttcttcca tttcaggtgt cgtgaggaat tcaccatgct gggcatctgg accctcctac      60
ctctggttct gactagtgtc gctactcaga acttggaagg cctgcatcat gatggccaat     120
tctgccataa gccctgtcct ccaggtgaaa ggaaagctag ggactgcaca gtcaatgggg     180
atgaaccaga ctgcgtgccc tgccaagaag ggaaggagta cacagacaaa gcccattttt     240
cttccaaatg cagaagatgt agattgtgtg atgaaggaca tggcttagaa gtggaaataa     300
actgcacccg gacccagaat accaagtgca gatgtaaacc aaactttttt tgtaactcta     360
ctgtatgtga acactgtgac ccttgcacca aatgtgaaca tggaatcatc aaggaatgca     420
cactcaccag caacaccaag tgcaaagagg aaggatccag atctaacgag cccaaatctt     480
gtgacaaaac tcacacatgc ccaccgtgcc cagcacctga actcctgggg ggaccgtcag     540
tcttcctctt ccccccaaaa cccaaggaca cctcatgat  ctcccggacc cctgaggtca     600
catgcgtggt ggtggacgtg agccacgaag accctgaggt caagttcaac tggtacgtgg     660
acggcgtgga ggtgcataat gccaagacaa agccgcggga ggagcagtac aacagcacgt     720
accgtgtggt cagcgtcctc accgtcctgc accaggactg gctgaatggc aaggagtaca     780
agtgcaaggt ctccaacaaa gccctcccag ccccatcga aaaaccatc tccaaagcca     840 aagggcagcc ccgagaacca caggtgtaca ccctgccccc atcccgggat gagctgacca     900
agaaccaggt cagcctgacc tgcctggtca aaggcttcta tcccagcgac atcgccgtgg     960
agtgggagag caatgggcag ccggagaaca actacaagac cacgcctccc gtgctggact    1020
```

```
ccgacggctc cttcttcctc tacagcaagc tcaccgtgga caagagcagg tggcagcagg    1080
ggaacgtctt ctcatgctcc gtgatgcatg aggctctgca caaccactac acgcagaaga    1140
gcctctccct gtctccgggt aaatgatagg gtaccttctg ag                       1182
```

<210> SEQ ID NO 19
<211> LENGTH: 531
<212> TYPE: DNA
<213> ORGANISM: Homo sapiens

<400> SEQUENCE: 19

```
ttttcttcca tttcaggtgt cgtgaggaat tcaccatgct gggcatctgg accctcctac     60
ctctggttct gactagtgtc gctactcaga acttggaagg cctgcatcat gatggccaat    120
tctgccataa gccctgtcct ccaggtgaaa ggaaagctag ggactgcaca gtcaatgggg    180
atgaaccaga ctgcgtgccc tgccaagaag ggaaggagta cacagacaaa gcccattttt    240
cttccaaatg cagaagatgt agattgtgtg atgaaggaca tggcttagaa gtggaaataa    300
actgcacccg acccagaat accaagtgca gatgtaaacc aaacttttt tgtaactcta     360 ctgtatgtga acactgtgac ccttgcacca aatgtgaaca tggaatcatc aaggaatgca    420
cactcaccag caacaccaag tgcaaagagg aaggatccag atctaacgag cccaaatctt    480
gtgacaaaac tcacacatgc ccaccgtgcc catagtgagg taccttctga g             531
```

<210> SEQ ID NO 20
<211> LENGTH: 335
<212> TYPE: PRT
<213> ORGANISM: Homo sapiens

<400> SEQUENCE: 20

```
Met Leu Gly Ile Trp Thr Leu Leu Pro Leu Val Leu Thr Ser Val Ala
  1               5                  10                  15

Arg Leu Ser Ser Lys Ser Val Asn Ala Gln Val Thr Asp Ile Asn Ser
             20                  25                  30

Lys Gly Leu Glu Leu Arg Lys Thr Val Thr Val Glu Thr Gln Asn
         35                  40                  45

Leu Glu Gly Leu His His Asp Gly Gln Phe Cys His Lys Pro Cys Pro
 50                  55                  60

Pro Gly Glu Arg Lys Ala Arg Asp Cys Thr Val Asn Gly Asp Glu Pro
 65                  70                  75                  80

Asp Cys Val Pro Cys Gln Glu Gly Lys Glu Tyr Thr Asp Lys Ala His
                 85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205
```

```
Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
        275                 280                 285

Glu Ala Tyr Asp Thr Leu Ile Lys Asp Leu Lys Lys Ala Asn Leu Cys
    290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335

<210> SEQ ID NO 21
<211> LENGTH: 144
<212> TYPE: PRT
<213> ORGANISM: Homo sapiens

<400> SEQUENCE: 21

Met Leu Gly Ile Trp Thr Leu Leu Pro Leu Val Leu Thr Ser Val Ala
1               5                   10                  15

Thr Gln Asn Leu Glu Gly Leu His His Asp Gly Gln Phe Cys His Lys
            20                  25                  30

Pro Cys Pro Pro Gly Glu Arg Lys Ala Arg Asp Cys Thr Val Asn Gly
        35                  40                  45

Asp Glu Pro Asp Cys Val Pro Cys Gln Glu Gly Lys Glu Tyr Thr Asp
    50                  55                  60

Lys Ala His Phe Ser Ser Lys Cys Arg Arg Cys Arg Leu Cys Asp Glu
65                  70                  75                  80

Gly His Gly Leu Glu Val Glu Ile Asn Cys Thr Arg Thr Gln Asn Thr
                85                  90                  95

Lys Cys Arg Cys Lys Pro Asn Phe Phe Cys Asn Ser Thr Val Cys Glu
            100                 105                 110

His Cys Asp Pro Cys Thr Lys Cys Glu His Gly Ile Ile Lys Glu Cys
        115                 120                 125

Thr Leu Thr Ser Asn Thr Lys Cys Lys Glu Glu Gly Ser Arg Ser Asn
    130                 135                 140

<210> SEQ ID NO 22
<211> LENGTH: 376
<212> TYPE: PRT
<213> ORGANISM: Homo sapiens

<400> SEQUENCE: 22

Met Leu Gly Ile Trp Thr Leu Leu Pro Leu Val Leu Thr Ser Val Ala
1               5                   10                  15

Thr Gln Asn Leu Glu Gly Leu His His Asp Gly Gln Phe Cys His Lys
            20                  25                  30

Pro Cys Pro Pro Gly Glu Arg Lys Ala Arg Asp Cys Thr Val Asn Gly
        35                  40                  45

Asp Glu Pro Asp Cys Val Pro Cys Gln Glu Gly Lys Glu Tyr Thr Asp
    50                  55                  60
```

-continued

```
Lys Ala His Phe Ser Ser Lys Cys Arg Arg Cys Arg Leu Cys Asp Glu
 65                  70                  75                  80

Gly His Gly Leu Glu Val Glu Ile Asn Cys Thr Arg Thr Gln Asn Thr
                 85                  90                  95

Lys Cys Arg Cys Lys Pro Asn Phe Phe Cys Asn Ser Thr Val Cys Glu
            100                 105                 110

His Cys Asp Pro Cys Thr Lys Cys Glu His Gly Ile Ile Lys Glu Cys
            115                 120                 125

Thr Leu Thr Ser Asn Thr Lys Cys Lys Glu Glu Gly Ser Arg Ser Asn
130                 135                 140

Glu Pro Lys Ser Cys Asp Lys Thr His Thr Cys Pro Pro Cys Pro Ala
145                 150                 155                 160

Pro Glu Leu Leu Gly Gly Pro Ser Val Phe Leu Phe Pro Pro Lys Pro
                165                 170                 175

Lys Asp Thr Leu Met Ile Ser Arg Thr Pro Glu Val Thr Cys Val Val
            180                 185                 190

Val Asp Val Ser His Glu Asp Pro Glu Val Lys Phe Asn Trp Tyr Val
            195                 200                 205

Asp Gly Val Glu Val His Asn Ala Lys Thr Lys Pro Arg Glu Glu Gln
210                 215                 220

Tyr Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Ala
                245                 250                 255

Leu Pro Ala Pro Ile Glu Lys Thr Ile Ser Lys Ala Lys Gly Gln Pro
            260                 265                 270

Arg Glu Pro Gln Val Tyr Thr Leu Pro Pro Ser Arg Asp Glu Leu Thr
            275                 280                 285

Lys Asn Gln Val Ser Leu Thr Cys Leu Val Lys Gly Phe Tyr Pro Ser
290                 295                 300

Asp Ile Ala Val Glu Trp Glu Ser Asn Gly Gln Pro Glu Asn Asn Tyr
305                 310                 315                 320

Lys Thr Thr Pro Pro Val Leu Asp Ser Asp Gly Ser Phe Phe Leu Tyr
                325                 330                 335

Ser Lys Leu Thr Val Asp Lys Ser Arg Trp Gln Gln Gly Asn Val Phe
            340                 345                 350

Ser Cys Ser Val Met His Glu Ala Leu His Asn His Tyr Thr Gln Lys
            355                 360                 365

Ser Leu Ser Leu Ser Pro Gly Lys
370                 375

<210> SEQ ID NO 23
<211> LENGTH: 159
<212> TYPE: PRT
<213> ORGANISM: Homo sapiens

<400> SEQUENCE: 23

Met Leu Gly Ile Trp Thr Leu Pro Leu Val Leu Thr Ser Val Ala
 1               5                  10                  15

Thr Gln Asn Leu Glu Gly Leu His His Asp Gly Gln Phe Cys His Lys
                 20                  25                  30

Pro Cys Pro Pro Gly Glu Arg Lys Ala Arg Asp Cys Thr Val Asn Gly
            35                  40                  45

Asp Glu Pro Asp Cys Val Pro Cys Gln Glu Gly Lys Glu Tyr Thr Asp
 50                  55                  60
```

```
Lys Ala His Phe Ser Ser Lys Cys Arg Arg Cys Arg Leu Cys Asp Glu
 65                  70                  75                  80

Gly His Gly Leu Glu Val Glu Ile Asn Cys Thr Arg Thr Gln Asn Thr
                 85                  90                  95

Lys Cys Arg Cys Lys Pro Asn Phe Phe Cys Asn Ser Thr Val Cys Glu
            100                 105                 110

His Cys Asp Pro Cys Thr Lys Cys Glu His Gly Ile Ile Lys Glu Cys
        115                 120                 125

Thr Leu Thr Ser Asn Thr Lys Cys Lys Glu Glu Gly Ser Arg Ser Asn
        130                 135                 140

Glu Pro Lys Ser Cys Asp Lys Thr His Thr Cys Pro Pro Cys Pro
145                 150                 155

<210> SEQ ID NO 24
<211> LENGTH: 10
<212> TYPE: PRT
<213> ORGANISM: Homo sapiens

<400> SEQUENCE: 24

Thr Gln Asn Leu Glu Gly Leu His His Asp
  1               5                  10

<210> SEQ ID NO 25
<211> LENGTH: 16
<212> TYPE: PRT
<213> ORGANISM: Homo sapiens

<400> SEQUENCE: 25

Met Leu Gly Ile Trp Thr Leu Leu Pro Leu Val Leu Thr Ser Val Ala
  1               5                  10                  15
```

FAS ANTIGEN DERIVATIVE

This application is a divisional of application Ser. No. 09/180,100, filed on Nov. 2, 1998 and now U.S. Pat. No. 6,306,395 and for which priority is claimed under 35 U.S.C. § 120. application Ser. No. 09/180,100 is the national phase of PCT International Application No. PCT/JP97/01502 filed on May 1, 1997 under 35 U.S.C. § 371. The entire contents of each of the above-identified applications are hereby incorporated by reference. This application also claims priority of Application No. 8-135760 filed in JAPAN on May 2, 1996 under 35 U.S.C. § 119.

TECHNICAL FIELD

This invention provides the field of medicaments with a novel Fas antigen derivative in which its activities and the like are improved and with a novel DNA fragment which encodes the same. The present invention also provides a recombinant DNA molecule which contains said DNA fragment, a transformant and a method for the production of said novel Fas antigen derivative.

BACKGROUND ART

Human Fas antigen is a polypeptide which is distributed in the surface of various cells and considered to be related to a type of the death of cells, called apoptosis. Homeostasis of the living body is skillfully regulated by the growth and differentiation of cells and the death thereof, and apoptosis is a mode of cell death which is discriminated from necrosis among modes of dying cells. It is known that the death of cells required for the maintenance of homeostasis of the living body, namely a case of cell death in which cells unnecessary for the living body are removed or virus-infected cells or tumor cells are attacked and removed by cytotoxic T lymphocytes (CTL) or natural killer (NK) cells, is mainly based on apoptosis.

It has been remained unexplained for a long time about the true character of Fas antigen which is a monoclonal antibody obtained by immunizing mice with human fibroblasts, originally found by Yonehara, S. et al. (*J. Exp. Med.*, vol. 169, pp. 1747–1756, 1989) as a cell surface antigen which is recognized by an anti-Fas antibody capable of inducing apoptosis in certain cells (Yonehara, S. et al.) and transfers a signal of apoptosis to the cells.

Recently, a Fas antigen gene has been cloned which revealed that the Fas antigen is a type I transmembrane glycoprotein which, according to its amino acid sequence, belongs to the NGFR (nerve growth factor receptor)/TNFR (TNF receptor) family that constitutes physiologically important cell surface membrane proteins (Itoh, N. et al., Cell, vol. 66, pp. 233–243, 1991). A mouse Fas antigen gene has also been cloned (Watanabe-Fukunaga, R. et al., *J. Immunol.*, vol. 148, pp. 1274–1279, 1992), which confirmed that Fas antigen mRNA is expressed in the thymus, liver, lung, heart and ovary of mouse. Its expression in human has also been reported in various tissues and cells such as lymphocytes, hepatocytes, small intestine epithelial cells, skin keratinocytes and osteoblasts (Leithauser, F. et al., *Lab. Invest.*, vol. 69, pp. 415–429, 1993)

The Fas antigen which was originally assumed to be present on the surface of cells has been detected in blood and culture supernatants, too, and its presence in the form of a soluble type Fas antigen (sFas) has also been found, so that their physiological functions and the like have become of interest in recent years.

Cheng, J. et al. (*Science*, vol. 263, pp. 1759–1762, 1994) have reported that they have found a mRNA molecule coding for a ΔTM type soluble form of Fas antigen, which seemed to encode a secretor molecule by the deletion of exon IV (corresponds to 14 base pairs of the extracellular region and 49 base pairs of the transmembrane region) due to alternative splicing, that concentration of the soluble type Fas antigen was high in sera of systemic lupus erythematosus (SLE) patients and that increase in the autologous mixed lymphocyte reaction was observed, together with increase in the number of splenocytes, when a chimera molecule composed of the extracellular region of mouse Fas antigen and the Fc moiety of human IgG was administered to mice. Also, Cascino, I. et al. (*J. Immunol.*, vol. 154, pp. 2706–2713, 1995) have reported that at least three Fas antigen-encoding mRNA molecules exist, including the just described Fas antigen mRNA. Though their physiological functions, expression regions and the like are still unclear, it has been shown that the recombinant ΔTM type Fas antigen inhibits the cytotoxic activity of Fas ligand in a concentration-dependent manner and that most of the soluble type Fas antigens existing in sera of healthy people and SLE patients are ΔTM type Fas antigens encoded by splicing variants (Kayagaki, N. et al., Igaku-no Ayumi (Advance in Medical Science), vol. 174, pp. 1136–1140, 1995).

In addition, Kimura, K. et al. have recently cloned a rat Fas antigen gene and reported that two types of Fas antigen mRNA can be detected in rat liver mRNA based on the alternative splicing and that a mRNA molecule which encodes a peptide having smaller molecular weight is present in addition to the mRNA of membrane binding type Fas antigen (*Biochemical and Biophysical Research Communications*, vol. 198 (2), pp. 666–674 (1994)) and also have isolated and identified mutants (variants) of corresponding human Fas antigen (Japanese Patent Application Kokai No. 7-289266).

On the other hand, human Fas ligand is a polypeptide that has been reported by Nagata et al. to be a biological molecule that induces apoptosis of Fas antigen-expressing cells (Takahashi, T. et al., *International Immunology*, vol. 6, pp. 1567–1574, 1994). Human Fas ligand is a Type II membrane protein of TNF family with a molecular weight of about 40 kD. As in the case of TNF, human Fas ligand in the human body is estimated to be in the form of a trimer (Tanaka, M. et al., *EMBO Journal*, vol. 14, pp. 1129–1135, 1995). The extracellular domain of the human Fas ligand is highly homologous with the extracellular domain of rat Fas ligand (Suda, T. et al., *Cell*, vol. 75, pp. 1169–1178, 1993) and mouse Fas ligand (Takahashi, T. et al., *Cell*, vol. 76, pp. 969–976, 1994). The human Fas ligand recognizes not only human Fas antigen but also mouse Fas antigen, and induces the apoptosis. On the other hand, the rat Fas ligand and the mouse Fas ligand recognize the human Fas antigen to induce the apoptosis.

Apoptosis has called attention for its deep involvement in homeostasis of an organism. The homology of the Fas ligands among different species as mentioned above suggests the important role of the apoptosis mediated by the Fas ligand and the Fas antigen in the homeostasis of organism.

Recently, an interesting relation of abnormality of Fas ligand and Fas antigen with an autoimmune disease has been reported. In this report, there is suggested that MRL-1pr/1pr (a strain of model mouse for an autoimmune digease) has mutation in its Fas antigen gene, and apoptosis is not induced in the cells expressing such mutant Fas antigen gene (Watanabe-Fukunaga, R. et al., *Nature*, vol. 356, pp. 314–317, 1993; Adachi, M. et al., Proc. *Natl. Acad. Sci. USA*, vol. 90, 1993). In the meanwhile, there has also been reported that C3H-gld/gld (another strain of model mouse for an autoimmune disease) has mutation in its Fas ligand gene, and that the Fas ligand of the gld mouse has no apoptosis-inducing activity. The mutation in the Fas ligand gene of the gld mouse is a point mutation, and as a result of such point mutation, $7^{th}$ amino acid from the C terminal of the extracellular domain of the Fas ligand is replaced with another amid acid (Tomohiro Takahashi, et al., *Cell*, vol. 76, pp. 969–976, 1994). The Fas ligand of the gld mouse as described above is incapable of binding with the Fas antigen (Fred Ramsdell, et al., *Eur. J. Immunol.*, vol. 24, pp. 928–933, 1994).

Also, in the case of SLE patients, increase in the level of a soluble type Fas antigen in blood (Cheng J. et al., *Science*, vol. 263, pp. 1759–1762, 1994) and increase in the expression of a Fas antigen on the surface of lymphocytes (Amasaki T. et al., *Clin. Exp. Immunol.*, vol. 99, pp. 245–250, 1995) have been reported, and it has been suggested about a possibility that abnormality of a Fas antigen gene accompanied by the abnormal expression and function of the Fas antigen is concerned also in lymphocytosis syndrome (Rieux Laucat et al., *Science*, vol. 268, pp. 1347–1349, 1995, and Fisher G. H. et al., *Cell*, vol. 81, pp. 935–946, 1995).

The finding as described above resulted in the hypothesis that some autoimmune diseases are induced by the abnormality of the Fas antigen or the Fas ligand, namely, by the autoreactive T cells remaining in the body that should have been removed from the body by undergoing apoptosis if the cells had been normal.

Recently, it is conceived that abnormal propagation and articular cytoclasis of synovial membrane that takes place in articular rheumatism is also induced by the failure of normal apoptosis of the cell. Kobayashi, N. et al. further estimates that reduction in the number of T cells upon infection by AIDS virus is mediated by the Fas ligand since expression of the Fas antigen on the T cell membrane is induced upon infection by the AIDS virus (*Nikkei Science*, vol. 6, pp. 34–41, 1993).

Participation of apoptosis by Fas ligand has been suggested also in viral fulminant hepatitis and the like diseases (Nagata, S. et al., *Immunol. Today*, vol. 16, pp. 39–43, 1995). Thus, as the relationship between Fas antigen-mediated apoptosis and diseases has been revealed, great concern has been directed toward the application of Fas ligand or Fas antigen to the treatment of diseases which are accompanied by abnormal apoptosis, namely the aforementioned autoimmune diseases, rheumatism, AIDS and the like.

Examples of the substance which inhibits Fas antigen-mediated apoptosis so far reported include a ΔTM type Fas antigen, a fusion protein of the extracellular region of Fas antigen with the Fc region of immunoglobulin G (IgG) and a fragment of anti-Fas antibody (Dhein J. et al., *Nature*, vol. 373, pp. 438–441, 1995) and an anti-Fas antagonist antibody (Alderson M. A. et al., *Int. Immunol.*, vol. 6, pp. 1799–1806, 1994).

Nagata et al. have also reported that they succeeded in obtaining an antibody against the Fas ligand, and that such antibody was capable of suppressing the apoptosis (Masato Tanaka, et al., EMBO Journal, vol. 14, pp. 1129–1135, 1995; International Patent Application Laid-Open No. WO95/13293).

As described in the foregoing, as Fas antigens have been isolated, it has been revealed that apoptosis is induced via these Fas antigens in the living body and the Fas antigen-mediated apoptosis is concerned in various diseases, so that it is considered that a substance capable of controlling the Fas antigen-mediated apoptosis will be useful in the prevention, treatment and diagnosis of diseases in which apoptosis is presumably concerned. Though usefulness of a pharmaceutical preparation in the living body should be evaluated by synthetically taking its activity, biological behavior, safety, side effects and the like into consideration, a substance having particularly high activity will exert its efficacy at a low dosage in the living body so that it will have high industrial availability. Because of this, great concern has been directed toward the development of an improved novel Fas antigen derivative, especially a Fas antigen derivative having more high activity, and the elucidation of its characteristics, particularly, when its application to the living body such as human treatment is taken into consideration, a novel Fas antigen derivative capable of controlling the Fas antigen-mediated apoptosis at more smaller dosage is expected from the viewpoint of efficacy and safety.

In addition, acquisition of a novel Fas antigen derivative is also important for the elucidation of, for example, interaction of Fas antigen and Fas ligand and mechanism of the Fas antigen-mediated apoptosis.

It is known that a polypeptide can show its activity even in the form of its partial fragment when the fragment preserve its intrinsic structure at the active site. On the contrary, however, many cases are also known in that the activity of a polypeptide is changed, or lost in an extreme case, by a mutation or deletion of even one amino acid in the polypeptide.

Thus, an object of the present invention is to provide the field of medicaments with a novel Fas antigen derivative whose activity and the like are improved and with a novel DNA fragment which encodes the same. The present invention also provides a recombinant DNA molecule and a transformant, which contains said DNA fragment, and a method for the production of said novel Fas antigen derivative.

DISCLOSURE OF THE INVENTION

Under the aforementioned situation, the inventors of the present invention have found that a novel Fas antigen derivative in which specified numbers of amino acid residues are deleted from the N-terminal region of Fas antigen shows improved activity or function in comparison with the prior art Fas antigen or Fas antigen derivative, and the present invention has been accomplished as a result of intensive efforts.

Thus, according to a first aspect of the present invention, there is provided a novel Fas antigen derivative, at least a novel Fas antigen derivative which comprises at least a part or entire portion of Fas antigen extracellular region polypeptide in which at least one amino acid residue is deleted from a group of amino acid residues starting from the N-terminal amino acid residue of the Fas antigen polypeptide to a cysteine residue most close to the N-terminal side (excluding said cysteine residue). It also provides a novel Fas antigen derivative according to the above wherein it contains a part or entire portion of Fas antigen extracellular region polypeptide in which at least one amino acid residue is deleted from the $1^{st}$ to $42^{nd}$ amino acid residues counting from the N-terminus of the SEQ ID NO:15 in the Sequence Listing, and a novel Fas antigen derivative according to the above wherein the number of deleted amino acid residues is 29 or more, particularly a novel Fas antigen derivative according to the above wherein the number of deleted amino acid residues is 29.

It also provides a novel Fas antigen derivative which is a novel Fas antigen variant of the aforementioned derivative wherein it comprises 1 or 2 or more parts of Fas antigen or is a fusion polypeptide that comprises either one of the novel Fas antigen variants and other (poly)peptide, particularly at least one (poly)peptide selected from the group consisting of the following peptides, which is contained in the C-terminal side of the novel Fas antigen derivative.

a. A part or entire portion of the hinge region of immunoglobulin.

b. A part or entire portion of the Fc fragment of immunoglobulin.

It also provides a novel Fas antigen derivative which is a polymer of the aforementioned novel Fas antigen derivative.

According to a second aspect of the present invention, there is provided a DNA fragment which comprises a DNA sequence coding for the aforementioned novel Fas antigen derivative, particularly a DNA fragment which comprises a DNA sequence described in the SEQ ID NOS:12, 13, and 14 of the Sequence Listing.

According to a third aspect of the present invention, there is provided a recombinant DNA molecule which comprises the nucleotide sequence of said DNA fragment.

According to a fourth aspect of the present invention, there is provided a transformant which is transformed with the just described novel recombinant DNA molecule.

According to a fifth aspect of the present invention, there is provided, among production methods of the aforementioned novel Fas antigen derivative, a method for the production of the aforementioned novel Fas antigen derivative, which comprises the steps of culturing the just described transformant and recovering and purifying the novel Fas antigen derivative from said culture mixture.

According to a sixth aspect of the present invention, there is provided a medicament which comprises the novel Fas antigen derivative of the first aspect or a physiologically acceptable salt thereof as its active ingredient.

According to a seventh aspect of the present invention, there is provided a method for the improvement of the activity or function of Fas antigen or Fas antigen derivative, which comprises deleting at least one of the amino acid residues starting from the N-terminal amino acid residue of the Fas antigen to a cysteine residue most close to the N-terminal side (excluding said cysteine residue).

In this connection, the known human Fas antigen contains an amino acid sequence deduced from the cDNA sequence shown in FIGS. 1 and 2 (SEQ ID NO:16). It is assumed that the antigen is present as a type I transmembrane protein composed of 319 amino acids as a result of the cutting of its signal peptide (SEQ ID NO:25) consisting of 16 residues from the amino acid sequence and that it has an extracellular region of 157 amino acids (from $1^{st}$ to $157^{th}$ residues), a transmembrane region of 17 amino acids (from $158^{th}$ to $174^{th}$ residues) and a cytoplasmic tail region of 145 amino acids (from $175^{th}$ to $319^{th}$ residues). The extracellular region of human Fas antigen has a function to bind to Fas ligand, and a polypeptide resulting from the expression of the extracellular region alone exists as a soluable type and shows an apoptosis inhibiting activity by binding to the Fas ligand. In addition, according to the computer analysis of the present invention which will be described later in detail, there is a possibility that the $43^{rd}$ cysteine residue counting from the N-terminus is forming a certain bonding with other amino acid residue, thereby contributing to the maintenance of the domain structure of Fas antigen extracellular region.

On the other hand, the cysteine residue most close to the C-terminus of the Fas antigen extracellular region also seems to be necessary for the structure maintenance, but, since the aforementioned α TM type Fas antigen binds to the Fas ligand, it is presumed that the 5 residues in the C-terminus, namely from the $153^{rd}$ glycine residue to the $157^{th}$ asparagine residues, are not necessary for the activity.

BRIEF DESCRIPTION OF THE DRAWINGS

FIG. 1 is a chart showing nucleotide sequence of a DNA fragment coding for human Fas antigen (residues 1 to 1094 of SEQ ID NO:16) and amino acid sequence deduced therefrom (residues 1 to 300 of SEQ ID NO:20). The symbol * shows possible N-glycosylation site, and the underlined part shows predicted transmembrane region.

FIG. 2 is a chart showing nucleotide sequence of a DNA fragment coding for human Fas antigen (residues 1095 to 2534 of SEQ ID NO:16) and amino acid sequence deduced therefrom (residues 301 to 335 of SEQ ID NO:20). The symbol * shows possible N-glycosylation site, and the underlined part shows predicted transmembrane region.

FIG. 3 is a chart showing partial nucleotide sequence in a vector containing a cDNA nucleotide sequence (SEQ ID NO:17) coding for shFas (nd29) which is one of the novel Pas antigen derivatives of the first aspect of the present invention, and amino acid sequence deduced therefrom (SEQ ID NO:21). The symbol * shows possible N-glycosylation site.

FIG. 4 is a chart showing partial nucleotide sequence in a vector containing a cDNA riucleotide sequence (SEQ ID NO:18) coding for shFas (nd29)-Fc which is one of the novel Fas antigen derivatives of the first aspect of the present invention, and amino acid sequence deduced therefrom SEQ ID NO:22. The symbol * shows possible N-glycosylation site.

FIG. 5 is a chart showing partial nucleotide sequence in a vector containing a cDNA nucleotide sequence (SEQ ID NO:19) coding for shFas(nd29)-hinge which is one of the novel Fas antigen derivatives of the first aspect of the present invention, and amino acid sequence deduced therefrom (SEQ ID NO:23). The symbol * shows possible N-glycosylation site.

FIG. 12 is a graph showing cell apoptosis inhibiting activity of hFas-Fc and shFas(nd29)-hinge.

FIGS. 15(a) to (c) are schematic illustrations showing comparison of amino acid sequences of human Fas antigen, human Fas antigen extracellular region (shFas), hFas-Fc, shFas(nd29)-Fc and shFas(nd29)-hinge.

BEST MODE OF CARRYING OUT THE INVENTION

Figure 6:
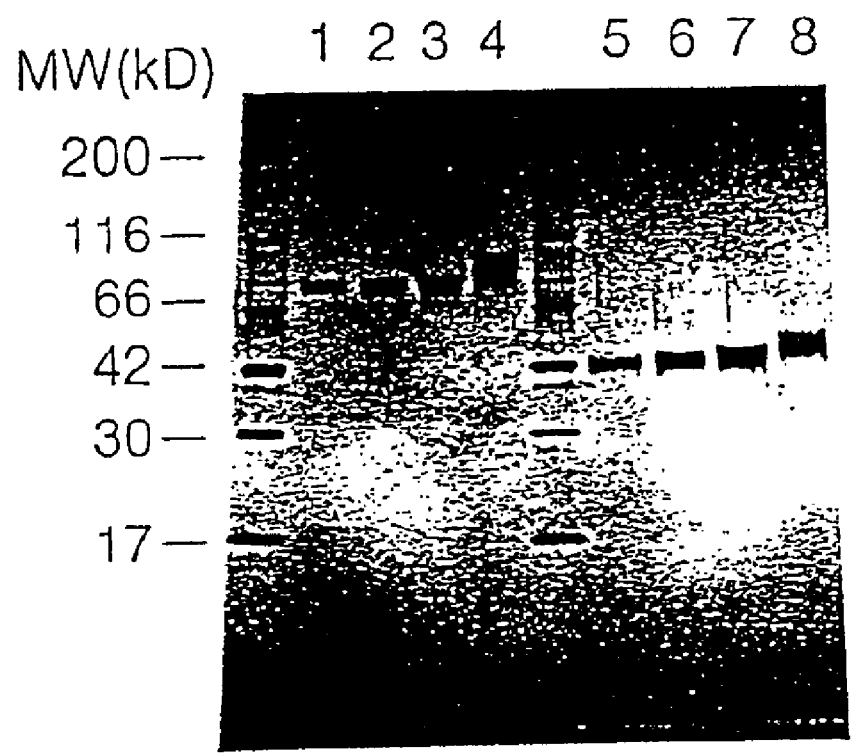
FIG. 6 is a photograph showing results of gel electrophoresis of shFas(nd29)-Fc and hFas-Fc.

The following describes the present invention in detail.

In the description of the novel Fas antigen derivative of the present invention, the term "a novel polypeptide containing an amino acid sequence (or (poly)peptide or the like)" has the following meaning. It means firstly that the novel polypeptide may be defined by its amino acid sequence, secondly that at least one optional amino acid may be added to either one or both of the N-terminus and C-terminus of the amino acid sequence and that, when the novel polypeptide is a fusion polypeptide or a polypeptide containing two or more functional regions, at least one optional amino acid may be added to (inserted into) their fused point or a site between the functional regions.

Also, the term "a polypeptide containing at least a part of an amino acid sequence (or (poly)peptide or the like)" means a novel polypeptide which contains entire portion of the amino acid sequence or a polypeptide that contains an optional partial sequence having an optional length of the amino acid sequence.

Also, in the description of the novel Fas antigen derivative of the present invention, the term "Fas antigen derivative" or "Fas antigen derivative polypeptide" means a polypeptide which contains at least a part of Fas antigen, and its examples include Fas antigen variants, a fusion polypeptide of Fas antigen or a Fas antigen variant with other (poly)peptide, and polymers thereof, as well as those which contain compounds other than the (poly)peptide.

The term "Fas antigen variant" or "Fas antigen variant polypeptide" as used herein means a polypeptide which comprises a part or two or more parts of Fas antigen, does not basically contain a (poly)peptide of other origin than Fas antigen and has at least one of the activities and functions of Fas antigen, and its examples include truncated Fas antigens and variants of Fas antigen in which one or more amino acids are deleted or substituted (to be referred to as deletion product or substitution product hereinafter in some cases), such as Fas antigens in which extracellular region, transmembrane region (like $\Delta$TM type Fas antigen (Fas $\Delta$TM)), or cytoplasmic tail region is deleted, and the like.

The term "fusion protein" as used herein means a polypeptide in which two or more (poly)peptides in a combination which does not exist naturally are linked to one another directly or indirectly, preferably directly, by chemical bonding, preferably peptide bonding.

The term "N-terminal region" at Fas antigen as used herein, in the case of the human Fas antigen (FIGS. 1 and 2) (SEQ ID NOS:16 and 20) for example, may include amino acid residues of the signal peptide (from −16 position Met to −1 position Ala in FIG. 1) (SEQ ID NO:25) in a broad sense, but, in the case of the novel Fas antigen derivative of the present invention, an N-terminal amino acid residue (Arg) resulting from the truncation of the signal peptide from the Fas antigen is used as the N-terminus, so that the term means a region starting from the N-terminal amino acid residue (Arg) and ending by an amino acid residue (42 position, Phe, of FIG. 1) just before the first cysteine residue (43 position, of FIG. 1).

Examples of the term "activity or function" as used herein include Fas ligand binding activity, biological activities such as apoptosis inhibiting activity, apoptosis inducing activity and the like which will be described later and functions resulting from stability, biological behavior, solubility and the like physico-chemical properties, of which Fas ligand binding activity and actions upon apoptosis are desirable and apoptosis inhibiting activity is particularly desirable.

In addition, the term "has an improved activity or function" as used herein means that at least one of the activity and the like values is at least larger, for example 1.4 times or more, preferably 2 times or more, more preferably 3 times or more, most preferably 5 times or more and most particularly preferably 10 times or more, than that of a polypeptide from which the corresponding N-terminal region is not deleted (N-terminal region non-deleted product). The activity values and the like can be measured by generally used methods and compared as their activity quantities per unit quantity, namely specific activities. The specific activity is generally calculated as 50% inhibition concentration ($IC_{50}$) or 50% effective dose ($ED_{50}$).

The novel Fas antigen derivative of the first aspect of the present invention is at least a novel Fas antigen derivative which at least comprises a part or entire portion of Fas antigen extracellular region polypeptide in which at least one amino acid residue is deleted from a group of amino acid residues starting from the N-terminal amino acid residue of the Fas antigen polypeptide to a cysteine residue most close to the N-terminal side (excluding said cysteine residue). In this connection, the just described part or entire portion of Fas antigen extracellular region polypeptide in which at least one amino acid residue is deleted and the novel Fas antigen derivative of the present invention are possessed of at least a function to bind to a Fas ligand.

Origin of the Fas antigen from which one or more amino acid residues are to be deleted is not particularly limited, but a mammal Fas antigen, particularly a human antigen such as an antigen which contains the known amino acid sequence of the human Fas antigen shown in FIGS. 1 and 2 is desirable.

When the Fas antigen from which one or more amino acid residues are to be deleted is the human Fas antigen shown in FIGS. 1 and 2, the novel Fas antigen derivative of the present invention is a novel Fas antigen derivative in which at least one amino acid residue is deleted from the $1^{st}$ to $42^{nd}$ amino acid residues counting from the N-terminus of the SEQ ID NO:15 (human Fas antigen extracellular region) in the Sequence Listing, preferably a novel Fas antigen derivative in which the number of deleted amino acid residues is 29 or more, more preferably 29.

The amino acids to be deleted may be continued or discontinued on the amino acid sequence but preferably continued, and, in that case, it is desirable to delete them preferentially from the N-terminal side. That is, a novel Fas antigen derivative in which 29 amino acid residues of from the $1^{st}$ to the $29^{th}$ positions counting from the N-terminus of the SEQ ID NO:15 of the Sequence Listing are deleted, so that it starts from the $30^{th}$ Thr residue, is particularly desirable.

Also, with regard to the number and position of N-terminal region amino acid residues desirable to be deleted, results of the three-dimensional structure analysis of Fas antigen extracellular region and the like by a computer can be used, which will be described in detail in Examples. That is, it is possible to optimize or control affinity and the like with a Fas ligand by designing the Fas antigen in the three-dimensional structure analysis in such a manner that the N-terminal region structure of the antigen does not cause steric hindrance for its binding with the Fas ligand.

In addition, there is a possibility that the N-terminal region of Fas antigen is apt to receive hydrolysis by protease and the like because of its structural characteristics. Also, since there is a possibility that processing of the polypeptide differs qualitatively or quantitatively depending on the host, these points and solubility, stability and the like can be taken into consideration when the N-terminal region is deleted.

When the above points are taken into consideration, the number of amino acid residues desirable to be deleted from the N-terminal region is preferably 13 to 18 or more, more preferably 23 or more, most preferably 29 or more, in the case of the human Fas antigen, and, in any case, it is desirable not to delete 36th to 42nd amino acid residues counting from the N-terminus.

With regard to the N-terminal region amino acid residues, particularly in the case of human Fas antigen, the novel Fas antigen derivative of the present invention includes a novel Fas antigen derivative which is a novel Fas antigen variant that comprises a part or entire portion of the Fas antigen extracellular region in which at least one amino acid residue is deleted from the $1^{st}$ to $42^{nd}$ amino acid residues counting from the N-terminus of the SEQ ID NO:15 in the Sequence Listing, particularly a novel Fas antigen variant which comprises 1 or 2 or more parts of the Fas antigen in which the number of deleted amino acid residues is preferably 29 or more, more preferably 29.

Illustrative examples of the Fas antigen variant of the present invention include those which contain a polypeptide of 158th to 174th residues, a polypeptide of 175th to 319th residues and a polypeptide of 158th to 319th residues, as well as a variant in which optional fragments having optional lengths obtained from the polypeptide of 158th to 319th residues are combined in optional order and included in the C-terminal or N-terminal side, preferably the C-terminal side, of the Fas antigen variant.

In this connection, the novel Fas antigen variant in which the number of deleted amino acid residues is 29 is preferably a variant that contains the amino acid sequence of SEQ ID NO:9 (shFas(nd29)) of the Sequence Listing, more preferably a variant which comprises said amino acid sequence.

Combined products with other chemical substances such as (poly)peptides, sugar chains, lipids or other high molecular weight or low molecular weight compounds and the like are included in the novel Fas antigen derivative, of which a fusion polypeptide with other (poly)peptide is desirable. Said (poly)peptide is not particularly restricted and two or more (poly)peptides may be included, and, in the latter case, binding order of said two or more (poly)peptides can be changed and substances other than amino acids may be included.

The bonding type of other chemical substances and the like with the essential novel Fas antigen variant is not particularly limited, and the bonding may be effected by any of covalent bonds and non-covalent bonds, but preferably by a covalent bond in view of the bonding stability. Particularly, peptide bond is desirable when the other chemical substance is a (poly)peptide.

The binding site can also be selected at will and any of the N-terminus, C-terminus and side chains can be used as the binding site, but the bonding may be effected mediated preferably by either one or both of the termini, more preferably by the C-terminus.

When the other chemical substance is a (poly)peptide, it is desirable that said (poly)peptide is a (poly)peptide which has an action to improve or modify activity or function of said novel Fas antigen derivative. For example, those which improve stability or half-life in blood or increase accumulation into specified tissues, cells or other specific regions are included, and Fc fragment can be cited as an example which can prolong blood half-life. Particularly preferred is a (poly)peptide which has such a function that said novel Fas antigen derivative becomes a polymer. Examples of the polymerizable (poly)peptide include entire portion or a part of the constant region of immunoglobulin heavy chain or light chain, entire portion or a part of the heavy chain constant region excluding its first region (CH1) and entire portion of the Fc fragment (it may comprise hinge region, CH2 region and CH3 region in the case of IgG) or a part thereof (for example, each of or an optional combination of hinge region, CH2 region, CH3 region and CH4 region), of which a portion that comprises the Fc fragment and at least a part of the hinge region is desirable, a portion of the hinge region which contains at least one, preferably all, of cysteine residues of the hinge region, or a Fc fragment containing said hinge region portion or CH3 region (CH4 region in the case of IgM and IgE) or a portion of hinge region is more desirable, and entire portion or a part of the Fc fragment containing the whole hinge region or the hinge region itself is most desirable.

The immunoglobulin of this case may be of any origin but preferably of human origin. Also, its class and subclass are not necessarily restricted, and any one of IgG1, IgG2, IgG3, IgG4, IgA1, IgA2, IgM, IgE and IgD and the like can be used, of which IgG is a preferred example. The novel Fas antigen derivative containing Fc fragment and the like can generally form a dimer, but it may also form a decamer when the original class is IgM or a tetramer in the case of IgA.

By the way, it is known that constant region, particularly Fc region, of immunoglobulin is important for various effector functions and the like of the antibody molecule, which are not directly concerned in the antigen specificity of the antibody. Examples of such functions include binding and activation of complements, binding with Fc receptors (FcR), induction of ADCC activity, placenta passing ability, degranulation of mast cells and protein A reactivity.

Though these functions can be utilized effectively when incorporated into the novel Fas antigen derivative of the present invention, they have a possibility to cause induction of side effects when administered to the living body as a medicament in certain cases, for example in a specific disease. In that case, therefore, an Fc fragment or the like from which all or a part of these effector functions and the like are removed is desirable, and its preferred examples include an Fc variant in which a mutation is introduced into the sugar addition site of the CH2 region of IgG, thereby deleting the sugar chain of said site, constant region or Fc fragment of IgG from which the CH2 region is deleted and hinge region.

In the novel Fas antigen derivative, binding of the novel Fas antigen variant with other (poly)peptide and the like may preferably be effected directly, but indirectly in some cases such as their bonding via a peptide linker or an appropriate chemical spacer which does not significantly spoil activities and functions of the novel Fas antigen derivative.

Activities and functions of the novel Fas antigen derivative of the present invention are further improved by its polymerization.

The polymer includes all of its dimer and more larger ones, but preferably dimer to decamer, more preferably dimer or trimer, most preferably dimer. It includes homo- and heteropolymers, but a homopolymer is more desirable.

With regard to the polymerization method, it is desirable to use polymerizing property of a (poly)peptide which by itself is polymerizable. A method in which the aforementioned polymerizing property of the constant region of immunoglobulin or its parts (Fc fragment and hinge region for example) is used is particularly desirable, but a cysteine-containing peptide which can form a hinge-like structure or a polypeptide which contains said peptide may also be used. In addition to the above, the cytoplasmic tail region of Fas antigen, TNF-R or the like may also be used. Though bonding of monomers in the polymer may be effected by any bond, a covalent bond (disulfide bond or peptide bond for example) is desirable, while a non-covalent bond (for example, bonding between two CH3 regions of immunoglobulin or between cytoplasmic tail regions of Fas antigen or TNF-R) can also be used.

In addition to the above, the following methods by chemical cross-linking can be employed. For example, 1) cysteine is introduced into the C-terminus and then cross-linking is effected using two types of activation linkers. There is a method for the introduction of cysteine in which cysteine amide or carboxypeptidase Y is used. When the C-terminus is lysine, lysine endopeptidase is used. Also, when free cysteine is present, protection is carried out in advance by alkylation prior to the introduction of cysteine into the C-terminus. Thereafter, cross-linking is carried out using activation linkers. For example, N,N'-o-phenylene dimaleimide (Glennie, M. J. et al., *J. Immunol.*, vol. 139, pp. 2367–2375, 1987) or the like as a divalent cross-linking agent and a trismaleimide compound (Japanese Patent Application Kokai No. 6-228091) or the like as a trivalent cross-linking agent have been used in the cross-linking of antibodies and can be applied to the novel Fas antigen derivative of the present invention to form a dimer and a trimer, respectively.

2) Biotin is introduced into the C-terminus and then cross-linking is carried out using avidin. It is introduced into the C-terminus using biotin amide similar to the case of cysteine. A tetramer is formed by the avidin cross-linking, but more higher aggregate may be formed depending on the reaction conditions. Also, other functional polypeptide or the like can be bound. The bond between biotin and avidin is an example of the strong non-covalent bonds.

3) Cross-linking is carried out using a cross-linking agent which is specific to cysteine, thiol or amino group present in the sequence of the novel Fas antigen derivative or (poly) peptide or the like linked to the derivative.

In the above cases, a peptide or chemical linker or a spacer having an appropriate length can be used.

Also, it is possible to make the novel Fas antigen derivative into liposomes by including lipid, hydrophobic peptide or the like fat-soluble substance according to known methods. For example, the novel Fas antigen derivative of the present invention which contains the transmembrane region of Fas antigen can be incorporated by itself into liposomes and the like. These liposomes are high degree polymers, and their appropriate modifications render possible further applications such as their incorporation into certain cells and tissues.

Among novel Fas antigen derivatives of the present invention, preferred examples having polymerization ability include those which contain the amino acid sequences of the SEQ ID NQS:10 (shFas(nd29)-hinge) and 11 (shFAS(nd29)-Fc) of the Sequence Listing, more preferably a derivative composed of said sequences.

Among the polymers of the polypeptides of the SEQ ID NOS: 10 and 11, the diner is a dimerization product of the Fas antigen derivative of the present invention in which its activities are improved by deleting 29 amino acid residues from the N-terminus of the extracellular region of the human Fas antigen, and the improved activities are not spoiled by the dimerization so that the resulting dimer is possessed of markedly high Fas ligand binding activity and apoptosis inhibiting activity.

In general, a polypeptide in different species or individuals generates different amino acid sequences caused by mutation during the process of its evolution while basically preserving original functions of the peptide. The term mutation of amino acid sequence as used herein means 1) deletion of one or more amino acid residues in the amino acid sequence of the polypeptide, 2) substitution by other amino acid residues or 3) insertion or addition of one or more amino acid residues into or to optional sites of the aforementioned amino acid sequence. Such mutations can be artificially generated using genetic engineering techniques, and polypeptides having such mutations are also included in the novel Fas antigen derivative of the present invention.

In addition, the novel Fas antigen derivative may have a methionine residue or one or more amino acid residues originated from a signal peptide or propeptide, added to the N-terminus.

The novel Fas antigen derivative of the first aspect of the present invention may have any modification with the proviso that its characteristics are not spoiled. Examples of the modification include modifications during or after translation of the polypeptide, which will usually occur in natural protein, and chemical modifications. Addition of sugar chain and the like can be cited as examples of the natural modification, N-glycosylation, O-glycosylation, non-enzymatic sugar addition and the like are known as the sugar addition to protein, and the novel Fas antigen derivative of the first aspect of the present invention may or may not have any sugar chain.

The novel Fas antigen derivative of the present invention may have N-glycosylation site(s), such as the case of the 29 N-terminal amino acid residues-deleted Fas antigen extracellular region which has two N-glycosylation sites. In consequence, said novel Fas antigen derivative may have sugar chains depending on the host which produces the derivative. That is, it is considered that the just described protein may have sugar chains on the aforementioned N-glycosylation sites when produced by using eucaryotic cells such as animal cells or yeast as the host cells, but may not have sugar chains when procaryotic cells such as Escherichia coli are used as the host. In addition, the number and length of the sugar chain or sugar composition and sequence of the sugar chain are not particularly limited, because they vary depending on the medium composition and the like at the time of the culturing of these host cells. Other examples of the natural modification include bonding of lipid and the like.

With the technical development in recent years, it became possible to modify polypeptide in various ways. Examples of the possible modification site include amino acid residues of the N-terminus or C-terminus and functional groups of the side chains. For example, it became possible to combine a polypeptide with polyethylene glycol, styrene-maleic acid copolymer, dextran, pyran copolymer, polylysine and the like synthetic high polymers, lipids, polysaccharides, (poly) peptides and the like natural molecules, hormones and the like physiologically active molecules or magnetite and the like inorganic substances (*Proc. Natl. Acad, Sci. USA*, vol. 84, pp. 1487–1491, (1981); *Biochemistry*, vol. 28, pp. 6619–6624 (1989)).

Examples of other modified derivatives include N-acyl derivatives of free amino group of an amino acid residue formed by the amido or acyl residue of carboxyl group resulting from the reaction of an aliphatic ester of carboxyl group with ammonia or a primary or secondary amine (an alkanoyl or carboxylaroyl group for example) and O-acyl derivatives of free hydroxyl group formed by an acyl residue (for example, hydroxyl group of serine or threonine residue).

The novel Fas antigen derivative of the present invention can also be modified in the aforementioned manner by the combination of the aforementioned known techniques. In consequence, products of such modifications are also included in the novel Fas antigen derivative of the present invention, with the proviso that characteristics of the polypeptide of the first aspect of the present invention are not spoiled. In addition, it is possible to modify or improve the activity or function of the novel Fas antigen derivative of the first aspect of the present invention, or to add or combine other activity or function, by such modifications. Examples of such activity or function include stability, solubility, biological behavior and directivity toward specified cells, tissues or organs. The novel Fas antigen derivatives which received such modifications are also included in the present invention.

The novel Fas antigen derivative of the present invention may exist in the form of salts which are also included in the present invention. The term "salts" as used herein means both of the salts of carboxyl groups of the protein molecule and acid addition salts to amino groups. The salts of carboxyl groups can be formed by the methods well-known in the field of these techniques, and their examples include inorganic salts such as salts of sodium, calcium, ammonium, trivalent iron, zinc and the like and organic salts such as those which are formed by triethanolamine, arginine, lysine, piperidine, procaine and the like. Examples of the acid addition salts include salts with hydrochloric acid, sulfuric acid and the like mineral acids and salts with acetic acid, oxalic acid and the like organic acids.

The novel Fas antigen derivative of the present invention can be applied to medicaments and, in that case, it is desirable that the aforementioned modification and the like techniques can keep pharmaceutical acceptability.

In addition, method for the production of the aforementioned novel Fas antigen derivative of the first aspect is not particularly limited, so that it may be isolated and purified from a natural source, artificially synthesized using a usually used chemical synthesizer (Peptide Synthesizer Model 430A, Perkin-Elmer Japan) or obtained by the recombinant DNA techniques. Also, the thus isolated and purified peptide may be subjected to an appropriate chemical treatment, such as an enzymatic treatment, to obtain deletion or fragmentation products which may further be linked together chemically or polymerized. That is, monomers of the novel Fas antigen derivative of the present invention are also useful as intermediates or intermediate materials for the production of polymers.

Among the aforementioned derivatives, a peptide produced by means of genetic engineering techniques, which will be described later as the fifth aspect of the present invention, is desirable from the viewpoint of the productivity and homogeneity or purity of the produced protein, such as its nature of being free from other contaminated human proteins.

An example of the production by genetic engineering techniques is briefly described in the following. The plasmid pM1097 which will be described later in Inventive Example 1 (1) contains a DNA fragment represented by the nucleotide sequence of SEQ ID NO:12 which encodes the amino acid sequence of the SEQ ID NO:9 shown in the Sequence Liasing and another DNA fragment that encodes the signal peptide of Fas antigen. Using an appropriate vector such as an expression vector shown in Examples constructed by integrating the just described plasmid into plasmid pM1103 prepared by integrating dhfr gene into pEF-BOS, COS-1 cells were transformed to obtain a transformant and then shFas(nd29) was obtained from its culture supernatant.

Among activities and functions of the novel Fas antigen derivative of the present invention, the apoptosis inhibiting activity can be examined by measuring inhibition ratio of Fas antigen expression cells to apoptosis. For example, it is measured by the $^{51}$Cr release assay or MTT assay (Mosmann T., *J. Immunol. Methods*, vol. 65, pp. 55–63, 1983) using a cultured cell strain or transformed cells capable of expressing Fas antigen as the target Fas antigen expression cells, and Fas ligand expressing cells obtained by transformation or a soluble type Fas ligand such as the Fas ligand extracellular region as the effector. Illustrative methods are shown in Examples. Apoptosis inhibiting activity of said novel Fas antigen derivative on WC 8 cells obtained by transforming mouse WR19L cells to give Fas antigen expressing ability is at least larger, for example 1.4 times or more, preferably 2 times or more, more preferably 3 times or more, most preferably 5 times or more and most particularly 10 times or more, than that of its corresponding N-terminal region non-deleted Fas antigen (derivative).

Since the novel Fas antigen derivative of the present invention can control Fas antigen-mediated apoptosis, it is useful for the prevention and treatment of diseases related to the sthenia or failure of Fas antigen-mediated apoptosis induced in the living body. For example, since a preferred novel Fas antigen derivative of the present invention can inhibit induction of apoptosis by competitively inhibiting bonding between Fas ligand and Fas antigen, it is possible to prevent reduction of functions of tissues and organs by inhibiting apoptosis of hepatic cells and the like in the case of hepatitis and the like serious infectious diseases and thereby preventing rapid reduction of cells in major organs and tissues, and it can be used for the treatment of infectious diseases caused by viruses and the like and complications thereof, for example as a drug for use in the treatment of influenza, AIDS, hepatitis and the like diseases. It is also useful for the treatment of certain autoimmune diseases such as diabetes, myocardiopathy in reperfusion injury and the like ischemic heart diseases, nephritis, multiple organ failure and organ preservation and graft versus host disease (GVHD) at the time of organ transplantation.

Since the novel Fas antigen derivative of the present invention binds to Fas ligand with more specific and high affinity, it can be used for the detection of Fas ligand. Also, since it keeps at least a part of the antigenicity of Fas antigen, it can bind to anti-Fas antibody and therefore is effective in inhibiting apoptosis caused by the anti-Fas antibody.

In addition, when Fas ligand itself is used in treatments and studies, it is necessary to produce said protein in a large amount with a high purity, and, since the novel Fas antigen derivative of the present invention can be used for the preparation of affinity chromatography columns, it is also useful in purifying Fas ligand and the like substances which bind to Fas antigen.

The second aspect of the present invention is a DNA fragment which encodes the novel Fas antigen derivative of the first aspect of the present invention.

In the description of the DNA fragments and DNA molecules in this specification, the term "a DNA fragment containing a nucleotide sequence" means that the DNA fragment may be a DNA fragment which comprises the nucleotide sequence or a fragment that comprises a variant of the nucleotide sequence in which at least one optional base is added to either one or both of its 5'-end and 3'-end.

The novel DNA fragments of the present invention contains at least a part of a nucleotide sequence which encodes the novel Fas antigen derivative of the first aspect of the present invention, preferably the amino acid sequences of the SEQ ID NOS:9, 10, and 11 of the Sequence Listing. Since it is generally known that there are 1 to 6 different DNA triplets (codons) which encode an amino acid depending on each amino acid, the DNA nucleotide sequences which encodes amino acid sequence of the novel Fas antigen derivative of the first aspect of the present invention are not limited to one type. In consequence, all DNA fragments comprised of every nucleotide sequence are included in the present invention, provided that they are DNA fragments which contain at least a part, preferably entire portion, of a nucleotide sequence which encodes the novel Fas antigen derivative of the first aspect of the present invention, preferably the amino acid sequences of the SEQ ID NOS:9, 10, and 11 of the Sequence Listing. The novel DNA fragment of the present invention is more preferably a DNA fragment which contains at least a part of the SEQ ID NOS:12, 13, and 14 of the Sequence Listing among the nucleotide sequences coding for the amino acid sequences of the SEQ ID NOS:9, 10, and 11 of the Sequence Listing, most preferably which contains all of the nucleotide sequences of the SEQ ID NOS:12, 13, and 14 of the Sequence Listing.

The DNA fragment of the present invention may be a cDNA molecule, a chromosomal DNA fragment, a combination thereof or a cDNA molecule which contains introns that can suitably be spliced. However, it is desirable that the DNA fragment of the present invention is a cDNA molecule because of its easiness to handle for genetic engineering techniques.

According to the present invention, it also provides an RNA molecule corresponding to the novel DNA fragment of the present invention and a DNA fragment containing a sequence complementary to the novel DNA fragment of the present invention and its corresponding RNA molecule. The novel DNA fragment of the present invention and its complementary DNA and RNA may form a double-stranded or triple-stranded chain through their mutual complementary bonding. Also provided are a DNA fragment which contains a nucleotide sequence capable of hybridizing with the novel DNA fragment of the present invention and its corresponding RNA molecule. In this case, they may also form a double-stranded or triple-stranded chain through their mutual bonding. In the above case, it may have inosine or the like universal base as a nucleic acid base.

The DNA fragment of the second aspect of the present invention may be obtained by any method. For example, it may be chemically synthesized, obtained from an appropriate DNA library or obtained by PCR (polymerase chain reaction) method using, as a template, a DNA fragment containing a DNA fragment which encodes whole length or a part of human Fas antigen. Also, the DNA fragments obtained by these methods or their smaller fragments may be further subjected to annealing and ligation as occasion demands.

The DNA fragment of the present invention can be synthesized chemically in the following manner. Illustratively, the DNA fragment of the present invention is divided into fragments of about 20 to 30 bases and synthesized as a plurality of fragments using a DNA synthesizer (for example, Model 394, manufactured by Applied Biosystems) and then each of the fragments is subjected to the phosphorylation of its 5'-end as occasion demands and then to annealing and ligation, thereby obtaining the DNA fragment of interest.

The DNA fragment of the present invention can also be obtained by PCR method using a genomic library, cDNA library or the like as the template. When PCR method is used, it can be obtained by preparing sense and antisense primers designed based on known nucleotide sequences and the nucleotide sequence of a DNA fragment which encodes the novel Fas antigen derivative of the first aspect of the present invention in combination, if necessary, with a restriction enzyme recognition sequence and the like, and then carrying out the reaction in accordance with the known method (cf. Polymerase Chain Reaction, PCR Protocols, a guide to methods and applications (1990), edited by Michael A. I. et al., published by Academic Press) on an optional DNA library or the like. Its typical example will be described in Examples.

The aforementioned DNA library is not particularly limited, with the proviso that it contains the DNA fragment of the second aspect of the present invention or a part thereof. In consequence, a commercially available DNA library may be used, or a cDNA library may be prepared in accordance with the method of Sambrook J. et al. from human peripheral blood lymphocytes, established human cell line, hybridoma and the like appropriate cells, if necessary activating them with an appropriate activating agent. In this connection, a transformant containing a DNA fragment coding for human Fas antigen has been deposited by the applicant of the present invention in National Institute of Bioscience and Human Technology, Agency of Industrial Science and Technology, the Ministry of International Trade and Industry, Higashi-1-1-3, Tsukuba-shi, Ibaraki, Japan (to be referred to as National Institute of Bioscience and Human Technology hereinafter) and has been assigned the designation as FERM BP-3826.

The novel DNA fragment of the second aspect of the present invention can be used in the preparation of the recombinant DNA molecule of the third aspect of the present invention and, by transforming a host with the recombinant DNA molecule, can be used for the humogenous and large scale production of the novel Fas antigen derivative of the first aspect of the present invention.

Because of this, it becomes possible to provide the field of medicaments with the novel Fas antigen derivative as a principal component of therapeutic drugs and diagnostic drugs. Method for the production of the novel Fas antigen derivative of the first aspect of the present invention making use of the novel DNA fragment of the present invention will be described later in relation to the fifth aspect of the present invention.

In addition, the DNA fragment of the second aspect of the present invention can be applied to the gene therapy of patients having hereditary or acquired abnormality in apoptosis mediated by Fas ligand or Fas antigen. That is, therapeutic and preventive treatments of patients suffering from articular rheumatism, SLE and the like autoimmune diseases and AIDS, hepatitis, nephritis and the like diseases can be carried out by connecting the novel DNA fragment of the present invention to an appropriate vector and introducing it directly into the living body or cells.

Next, the recombinant DNA molecule of the third aspect of the present invention is described. The recombinant DNA molecule of the third aspect of the present invention is characterized in that it contains the aforementioned novel DNA fragment of the second aspect of the present invention.

The novel recombinant DNA molecule of the present invention may be in any form such as cyclic, linear, single-stranded, double-stranded or a complex chain thereof, which can be selected at will depending on each purpose, but a cyclic form is desirable in view of easy handling and easy integration into host cells and a double-stranded form is desirably from the stability and the like point of view.

The novel recombinant DNA molecule of the present invention may be a molecule in which one or more optional bases are added to either one or both of the 5'-end and 3'-end of the nucleotide sequence of the DNA fragment of the second aspect of the present invention.

The bases to be added are not particularly limited, provided that they do not cause shifting of coding frame in the novel DNA fragment of the present invention, and their examples include an adapter sequence, a linker sequence or a nucleotide sequence which encodes a signal sequence, a nucleotide sequence which encodes β-galactosidase or the like other polypeptide and a sequence which is added when a DNA probe or the like is prepared, for the purpose of increasing its detection sensitivity.

It is desirable that the recombinant DNA molecule of the present invention contains other nucleotide sequences as occasion demands, in addition to the novel DNA fragment of the second aspect of the present invention. The term "other nucleotide sequences" as used herein means for example an enhancer sequence, a promoter sequence, a ribosome binding site sequence, a nucleotide sequence which is used with the aim of amplifying DNA copy numbers, a translation initiation codon, a nucleotide sequence which encodes a signal peptide, a nucleotide sequence which encodes other polypeptide, a translation termination codon, a poly(A) addition sequence, a spliced sequence, a replication origin and a gene sequence to be used as a selection marker.

Though selection of necessary nucleotide sequences is decided based on the use of the recombinant DNA molecule to be prepared, they are preferably those which can transform host cells to give them the ability to produce the novel Fas antigen derivative of the first aspect of the present invention, so that said recombinant DNA molecule may preferably contain at least a translation initiation codon, a termination codon, a replication origin and a sequence of a selection marker gene, in addition to the novel DNA fragment of the second aspect of the present invention, and it may contain more preferably a promoter sequence which functions in the host cells. Particularly, it is desirable to add a sequence which encodes a signal peptide in addition to these sequences, because such a sequence renders possible transformation of host cells such that the novel Fas antigen derivative of the first aspect of the present invention can be expressed and secreted. For example, when a recombinant DNA molecule is prepared by connecting a DNA fragment containing entire portions of the nucleotide sequences of the SEQ ID NOS:12, 13, and 14 of Sequence Listing in an appropriate vector to the downstream of a signal sequence coding for a signal peptide, and an appropriate host is transformed with the thus prepared molecule, culturing of the resulting transformant renders possible secretion of a polypeptide containing the amino acid sequences described in the SEQ ID NOS:9, 10, and 11 of Sequence Listing into the culture supernatant. Though the signal sequence to be connected can be selected optionally, a signal sequence which encodes the signal peptide of a Fas antigen, particularly human Fas antigen, is desirable, such as a signal sequence (residues 36 to 83 of SEQ ID NO:170 which encodes the signal peptide (SEQ ID NO:25) of human Fas antigen shown in FIG. 1 or FIG. 3.

In addition to the above, other suitable sequences can be used depending on the host and conditions to be employed, by selecting them from sequences which encode for example the signal peptide of TNF or G-CSF, the signal peptide of *E. coli* alkaline phosphatase, the signal peptide of yeast PHO1 and the signal peptide of yeast α-factor.

Examples of the selection marker gene include ampicillin resistance gene, kanamycin resistance gene, neomycin resistance gene, thimidine kinase gene and the like, and the novel recombinant DNA molecule containing at least two selection markers is desirable because of the reason that clones transformed with the gene of interest can be selected easily when yeast and mammal cells are used as the host. With regard to the sequence which is used for the purpose of amplifying copy numbers, sequences of dihydrofolate reductase gene (dhfr) and the like can be used.

Examples of the promoter sequence which functions in host cells include sequences of trp promoter and lac promoter when the host is *E. coli*, and sequences of alcohol oxidase 1 (AOX 1) promoter, polyhedrin promoter, SV40 promoter, SRα promoter and human elongation factor 1α (EF 1α) promoter when the host is yeast, COS cells or the like eucaryotic cells.

Preferred examples of the recombinant DNA molecule of the present invention, from the viewpoint of the host, include those which can transform *E. coli* cells such that the novel Fas antigen derivative of the first aspect of the present invention can be expressed. In consequence, it is desirable that the recombinant DNA molecule of the present invention is possessed of at least a promoter sequence which functions in *E. coli* cells, in addition to a replication origin and a marker sequence of *E. coli*, more desirably further having a sequence which encodes a signal peptide.

The trp promoter, lac promoter or the like is desirable as the suitable promoter sequence which functions in *E. coli* cells, and the signal peptide of *E. coli* alkaline phosphatase is desirable as the signal peptide which functions in *E. coli* cells.

More preferred example are those which can transform animal cells, yeast and the like eucaryotic cells thereby enabling the cells to express the novel Fas antigen derivative of the first aspect of the present invention. In this case, a suitable example of the recombinant DNA molecule of the present invention may have at least a poly(A) addition sequence in addition to a translation initiation codon, termination codon and a selection marker gene, as well as SV40 promoter, human elongation factor 1α (EF 1α) promoter or SRα promoter which functions in animal cells, alcohol oxidase 1 (AOX 1) promoter which functions in yeast and the SV40 replication origin.

The recombinant DNA molecule of the third aspect of the present invention can be obtained for example by a method in which the novel DNA fragment of the second aspect of the present invention is allowed to undergo ligation with other DNA fragment having an optional nucleotide sequence or a method in which said fragment is introduced into an optional vector (cf. Sambrook J. et al., Molecular Cloning, a Laboratory Manual, 2nd ed., Cold Spring Harbor Laboratory, New York, 1989).

Illustratively, the DNA fragment and a vector are respectively digested with appropriate restriction enzymes, and the thus obtained fragments are subjected to ligation using a DNA ligase. The vector may be any one of plasmid vectors, phage vectors, virus vectors and the like, and a commercially available article may also be used. Examples of typical vectors include pUC118, pBR322, pSV2-dhfr, pBluescriptII, PHIL-S1, λZapII, λgt10, pAc700, YRP17, pEF-BOS, pEFN-II and the like, of which pEF-BOS or the like is desirable because of its capability to perform high expression.

In addition, the recombinant DNA molecule of the third aspect of the present invention may be used in any application. For example, it may be used when the novel Fas antigen derivative of the first aspect of the present invention is produced in an industrial scale or for the purpose of producing the novel DNA fragment of the second aspect of the present invention in a large scale by its amplification. Also, the recombinant DNA molecule of the third aspect of the present invention can be used for the preparation of the transformant of the fourth aspect of the present invention.

Next, the transformant of the fourth aspect of the present invention is described. The transformant of the present invention is characterized in that it is transformed with the recombinant DNA molecule of the third aspect of the present invention. In other words, the transformant of the present invention can be obtained by introducing the recombinant DNA molecule of the third aspect of the present invention into cells or a microorganisms to be used as the host.

The transformant of the present invention is obtained by transforming either procaryotic cells or eucaryotic cells. Examples of the procaryotic cells include cells of *E. coli*, *Bacillus subtilis* and the like. Examples of the eucaryotic cells include COS cells, CHO cells, HeLa cells, Namalwa cells and the like mammal cells, as well as Sf cells and the like insect cells and yeast cells. Among these hosts, *E. coli* cells, mammal cells or yeast cells are desirable, because transformants obtained by transforming these cells are easy to handle and high expression quantity can be expected therefrom.

Since copy number of the gene can be increased in mammal cells, it is desirable to use dhfr-defective CHO cells as the host. Also, since the amount of secretion production of exogenous proteins is large in yeast cells, it is desirable to use a yeast of the genus *Pichia* as the host.

In order to exert functions of the recombinant DNA molecule of the present invention sufficiently, a vector to be used in the preparation of the recombinant DNA molecule of the present invention should be suited for the host cells. Examples of the desirable combination of the vector used in the recombinant DNA molecule with the host include pUC118 with *E. coli*, pEF-BOS with COS cells or CHO cells, Yac with yeast cells and AcNPV with Sf cells (cf. Genetic Engineering Handbook, a special issue of *Experimental Medicine*, published by Yodo-sha, Japan, Mar. 20, 1991). In the same manner, the promoter, a signal peptide encoding nucleotide sequence, marker genes and the like to be contained in the recombinant DNA molecule should be used by selecting those which are suited for the host to be used.

Also, in order to obtain a transformant capable of expressing the novel Fas antigen derivative of the first aspect of the present invention, said recombinant DNA molecule should have a sequence which is necessary for the expression, such as an appropriate promoter or the like.

In order to obtain a transformant capable of secreting and producing the novel Fas antigen derivative of the first aspect of the present invention, host cells are transformed with a recombinant DNA molecule which is the aforementioned recombinant DNA molecule of the third aspect of the present invention suited for the production, namely a molecule in which a nucleotide sequence which encodes a signal peptide is included in the upstream of the DNA fragment of the second aspect of the present invention.

With regard to the method for introducing the recombinant DNA molecule of the third aspect of the present invention into host cells, a method suitable for the host or recombinant DNA molecule may be selected for example from an electroporation method, a protoplast method, an alkali metal method, a calcium phosphate method, a DEAE-dextran method, a microinjection method, a method in which infection is effected using virus particles and other known methods (cf. Genetic Engineering Handbook, a special issue of *Experimental Medicine*, published by Yodo-sha, Japan on Mar. 20, 1991). Since the transformation efficiency of mammal cells becomes high when the calcium phosphate method or DEAE-dextran method is used, it is desirable to use these methods when the host cells are mammal cells.

The transformant of the present invention is preferably a transformant which can express the novel Fas antigen derivative of the first aspect of the present invention, more preferably which can express said polypeptide and secrete it in the culture supernatant. The use of such a transformant facilitates large scale production of the novel Fas antigen derivative of the present invention.

Though the transformant of the fourth aspect of the present invention may be used for any purposes, it can be used for the purpose of producing the DNA of the second aspect of the present invention or the recombinant DNA molecule of the third aspect of the present invention in a large amount and of producing the novel Fas antigen derivative of the first aspect of the present invention in an industrial scale.

The production method of the fifth aspect of the present invention is a method for the production of the novel Fas antigen derivative of the first aspect of the present invention, which is characterized by the use of the transformant of the fourth aspect of the present invention. According to the production method of the present invention, the transformant of the fourth aspect of the present invention is cultured and, if necessary, amplification and expression induction of the gene are carried out. Thereafter, the resulting culture mixture is recovered and then, as occasion demands, purification of the novel Fas antigen derivative of the present invention is carried out by optionally combining concentration, solubilization, dialysis, various chromatographic techniques and the like means.

In the fifth aspect of the present invention, the term "culture mixture" means a transformant, a medium containing the transformant, culture supernatant or a lysate of the cells. When the produced aforementioned novel Fas antigen derivative is secreted into cell culture supernatant, said polypeptide can be purified from the culture supernatant. On the other hand, when the novel Fas antigen derivative is accumulated in cells of the transformant, the cells are dissolved or disrupted by optionally selecting a method suitable for the host cells from lysozyme treatment, detergent treatment, freeze-thawing, pressurization, ultrasonication and other methods, and then said polypeptide is recovered as a soluble fraction or insoluble fraction and purified.

When the host is *E. coli* cells and the aforementioned novel polypeptide is accumulated into periplasm, said polypeptide can be recovered by employing the method of Willsky et al. (*J. Bacteriol.*, vol. 127, pp. 595–609, 1976).

Culturing of the transformant can be carried out in the usual way with reference to various textbooks (cf. "Methods for Microbial Experiments", edited by Japanese Biochemical Society, published by Tokyo Kagaku Dojin, 1992).

When expression induction of the gene is carried out, an appropriate agent is selected and used depending on the integrated promoter. For example, 3β-indoleacrylic acid may be used when trp promoter is integrated, dexamethasone may be used in the case of MMTV promoter, and methanol in the case of AOX1 promoter.

A typical example of the gene amplification method is a method in which dhfr-deficient CHO cells are used as the host and methotrexate is used when a dhfr-containing vector is used.

The transformant to be used in said production method is not particularly limited, provided that it is the transformant of the fourth aspect of the present invention, but it is desirably a transformant obtained using a host selected from COS cells, CHO cells and the like mammal cells, yeast cells and $E.$ $coli$ cells.

The following shows examples of the culturing and expression induction when $E.$ $coli$, CHO cell or the like mammal cell or a yeast of the genus $Pichia$ is used as the transformant.

In the case of $E.$ $coli$ transformed with a recombinant DNA molecule having trp promoter, the cells are pre-cultured in L-broth and then inoculated into M9-CA medium in an inoculum size of 1/50 volume to carry out culturing at 37° C. When the OD550 value reached 1 to 4 (namely the logarithmic growth phase) several hours after commencement of the culturing, 3β-indoleacrylic acid is added to a final concentration of 10 μg/ml to carry out expression induction. By further carrying out about 1 to 2 days of culturing, a culture mixture containing the protein of interest can be obtained.

When a yeast of the genus $Pichia$ transformed with a recombinant DNA molecule having AOX1 promoter is used, the yeast is pre-cultured for about 2 days using BMGY medium, the medium is exchanged and then expression induction is effected by adding methanol. By further carrying out about 1 to 2 days of culturing at 30° C., a culture mixture containing the protein of interest can be obtained.

A transformant obtained by transforming CHO cells or the like mammal cells with a recombinant DNA molecule having the elongation factor promoter is cultured using DMEM medium containing 10% fetal calf serum. The cells are inoculated at a concentration of about $1–10\times10^4$ cells/ml and cultured at 37° C. in an atmosphere of 5% carbon dioxide/95% air. Since the cells generally become a confluent state 2 to 3 days thereafter, the medium is changed to serum-free D-MEM at that stage. By further carrying out 2 to 3 days of culturing, a culture mixture containing the protein of interest can be obtained. In this connection, when the amount of the produced protein of interest is small, it is possible to increase the production by amplifying the gene with methotrexate as described in the foregoing.

Purification of the novel Fas antigen derivative of the first aspect of the present invention from the aforementioned culture mixture is carried out by optionally selecting appropriate means from those which are generally used in the purification of polypeptides. Illustratively, the purification may be carried out by optionally combining appropriate means selected from usually used techniques such as salting-out, ultrafiltration, isoelectric precipitation, gel filtration, electrophoresis, ion exchange chromatography, hydrophobic chromatography, antibody chromatography and the like various affinity chromatographic techniques, chromatofocasing, adsorption chromatography, reverse phase chromatography and the like, if necessary further using a HPLC system and the like. Particularly, an affinity chromatography which uses an anti-Fas antibody capable of recognizing the novel Fas antigen derivative of the present invention, a Fas ligand, protein A or the like as the ligand is also useful for the purification of said novel polypeptide.

In said production method, the novel Fas antigen derivative of the first aspect of the present invention may be expressed as a fusion protein with $E.$ $coli$ β-galactosidase or other polypeptide, but, in that case, it is necessary to employ a step to cut off said protein by its treatment with cyanogen bromide, hydroxylamine or the like chemical substance or a protease or the like enzyme in any one of the purification steps.

Also, when the used transformant is $E.$ $coli$ and said protein is produced as an insoluble protein in the form of inclusion body, a procedure in which the inclusion body is subjected to solubilization, denaturation and refolding in that order may be carried out in an appropriate step of the purification (Thomas E. and Creighton J., $J.$ $Molecular$ $Biology$, vol. 87, pp. 563–577, 1974).

Illustratively, the cells are disrupted and centrifuged and the resulting pellet is recovered. Next, a solubilization buffer containing appropriate amounts of urea or guanidine hydrochloride and a detergent, reduced form glutathione and oxidized form glutathione (for example, a buffer containing 5 M guanidine hydrochloride, 0.005% Tween 80, 50 mM Tris-HCl (pH 8.0), 5 mM EDTA, 2 mM reduced form glutathione and 0.02 mM oxidized form glutathione) is added to the pellet, the mixture is subjected to denaturation by adding 2-mercaptoethanol and then the resulting sample is subjected to refolding by dialyzing it against the solubilization buffer from which guanidine hydrochloride is eliminated in advance. When the product is expressed as a fusion protein, unnecessary moiety of the protein is cut off using cyanogen bromide or the like chemical substance or a protease or the like enzyme after these treatments and then an appropriate chromatography is carried out.

According to said production method, the novel Fas antigen derivative of the present invention having Fas antigen activities, which is useful in pharmaceutical preparations and the like, can be produced homogenously with high efficiency in an industrial large scale.

Next, the medicament of the sixth aspect of the present invention is described. The medicament of the sixth aspect of the present invention contains the novel Fas antigen derivative of the first aspect or a physiologically acceptable salt thereof as its active ingredient.

Also, it can be made into a pharmaceutical composition by optionally adding pharmaceutically acceptable carriers, fillers, stabilizers, lubricants, coloring agents, disintegrating agents, antiseptics, tonicity agents, stabilizing agents, dispersing agents, antioxidants, buffers, preservatives, suspending agents, emulsifying agents and generally used appropriate solvents (sterilized water, plant oil and the like), as well as physiologically acceptable solubilizing agents and the like.

The medicament of the present invention can be used in various routes of administration of which parenteral administration is desirable. Examples of the parenteral administration include intravenous administration, intra-arterial administration, subcutaneous administration, intramuscular administration and the like injections which are general, as well as rectal administration, percutaneous absorption, transmucosal absorption and the like. In this case, suppositories, inhalations, particularly injections and the like are desirable as the dosage form.

The medicament of the sixth aspect of the present invention can control excess apoptosis and therefore can prevent and treat various morbid states and diseases caused by abnormal apoptosis, by administering it to humans or animals suffering from abnormal Fas antigen-mediated apoptosis, particularly excess apoptosis induced by overproduction of endogenous Fas ligand under morbidity or overdose of exogenous Fas ligand. Effective content or dosage and formulation of the novel Fas antigen derivative or a physiologically acceptable salt thereof as the active ingredient are optionally decided depending on the morbid state.

The seventh aspect of the present invention is a method for improving the activity or function of the Fas antigen or Fas antigen derivative, which is characterized by the deletion of at least one of the amino acid residues starting from the N-terminal amino acid residue of the Fas antigen to a cysteine residue most close to the N-terminal side (excluding said cysteine residue). It also provides a method for designing, or a method for preparing, the Fas antigen or Fas antigen derivative having improved activity or function, which is characterized by the deletion of at least one of the 1st to 42nd amino acid residues counting from the N-terminus of the Fas antigen. Said preparation method comprises the steps of producing the novel Fas antigen derivative of the first aspect of the present invention and confirming the improvement by measuring its activity and the like. A method for selecting amino acid residues to be deleted from the N-terminal region, a method for producing a polypeptide having said deletion and a method for measuring the activity are as described in the foregoing.

EXAMPLES

The following examples are provided for further illustration of the present invention, but the examples are for purpose of illustration only and are not intended as a definition of the limits of the invention. Also, the abbreviations used in the following description are based on the commonly used abbreviations in said field. In this connection, various procedures employed in the following examples were carried out mainly with reference to the journals and books shown below.

1. Michael A. I. et al., Polymerase Chain Reaction, PCR Protocols, a guide to methods and applications (1990), Academic Press 2. Sambrook J. et al., Molecular Cloning, 2nd ed., Cold Spring Harbor Laboratory, New York, 1989

3. Genetic Engineering Handbook, a supplement of *Experimental Medicine*, published by Yodo-sha, Japan, on Mar. 20, 1991

4. "Methods for Microbial Experiments", edited by Japanese Biochemical Society, published by Tokyo Kagaku Dojin, 1992

5. Methods for Immunological Experiments, edited by The Japanese Society for Immunology, published by The Japanese Society for Immunology 6. Fumio Imamoto et al., "Introduction of Recombinant Genes into Cells and their Expression", *Protein, Nucleic Acid and Enzyme*, Supplement 28(14), 1983

7. Yoshio Okada, "General Cell Technology Techniques", *Experimental Medicine*, Supplement 7(13), 1989

Inventive Example 1

Preparation of Novel Polypeptide Expression Vector (1) Preparation of Plasmid pM1097

Sense primer 1 (CTGACTAGTGTCGCTACTCAGAAC TTGGAA) and antisense primer 2 (GTCAAGCTTGGTAC CTATTAGTTAGATCTGGATCCTTC) were chemically synthesized (SEQ ID NOS:1 and 2 in the Sequence Listing, respectively). This sense primer 1 contains SpeI site (ACTAGT), 3'-end region of a nucleotide sequence which encodes the human Fas antigen signal peptide and a nucleotide sequence that encodes $30^{th}$ and $34^{th}$ amino acids of human Fas antigen. On the other hand, the antisense primer 2 contains a nucleotide sequence which encodes the C-terminal side of the human Fas antigen extracellular region, HindIII site (AAGCTT) and KpnI site (GGTACC).

A 100 µl portion of a solution was prepared which contained 100 pmol of each of the thus obtained sense primer 1 and antisense primer 2, 0.5 µg of a plasmid pBLF58-1 which contains a DNA fragment coding for the human Fas antigen (Itoh N. et al., Cell, vol. 66, pp. 233–243, 1991), 20 nmol of each of dATP, dCTP, dGTP and dTTP, and 2.5 units of Pfu DNA polymerase and 10 µl of attached Pfu buffer (both manufactured by Stratagene). Using a DNA Thermal Cycler (PCR System 9600, manufactured by Perkin-Elmer Corp.), 30 cycles of PCR was carried out, each cycle being 30 seconds at 94° C., 30 seconds at 55° C. and 1 minute at 72° C. The thus obtained PCR product was double-digested with SpeI and HindIII, the resulting DNA fragment of about 410 bp was intergrated into SpeI, HindIII site of a plasmid pM1081 containing a DNA fragment disclosed in Example 21 of International Patent Application WO 95/13293, which encodes the human Fas antigen signal peptide and human Fas ligand extracellular region, and the thus obtained plasmid was named pM1097. This plasmid contains a DNA fragment represented by the nucleotide sequence of SEQ ID NO:12 of the Sequence Listing.

(2) Preparation of Plasmid pM1303

Firstly, sense primer 3 (TCACAAGCCCAGCAACACC AAG), antisense primer 4 (GCTTGCCGGCCGTCGCACT C), sense primer 5 (GAAGGATCCAGATCTAACGAGCC CAAATCTTGT) and antisense primer 6 (GTCGGTACCCTATCATTTACCCGGAGACAG) were chemically synthesized (SEQ ID NOS:3, 4, 5, and 6 in the Sequence Listing, respectively). The sense primer 3 contains a nucleotide sequence which encodes C-terminal side of the CHi region of human immunoglobulin G1, and the antisense primer 4 contains a sequence that encodes 3'non-translation region of human immunoglobulin G1. The sense primer 5 contains a nucleotide sequence which encodes C-terminal side amino acids of the human Fas antigen extracellular region, a nucleotide sequence that encodes N-terminal side amino acid sequence of the hinge region of human immunoglobulin G1 and BamHI site (GGATCC). The antisense primer 6 contains a nucleotide sequence which encodes a C-terminal side amino acid sequence of the CH3 region of human immunoglobulin G1 and KpnI site (GGTACC). The PCR reaction was carried out under the same conditions of the step (1) by preparing 100 µl of a solution which contains 100 pmol of each of the thus obtained sense primer 3 and antisense primer 4, 1 µl of Human Spleen 5'-Stretch cDNA Ubrary (manufactured by Clontech), 20 nmol of each of dATP, dCTP, dGTP and dTTP, and 2.5 units of Pfu DNA polymerase and 10 µl of the attached Pfu buffer. Using the thus obtained PCR product of about 750 bp as the template, the PCR reaction was carried out in the same manner as described in the step (1) by preparing 100 μl of a solution which contains 100 pmol of each of the sense primer 5 and antisense primer 6, 20 nmol of each of dATP, dCTP, dGTP and dTTP, and 2.5 units of Pfu DNA polymerase and 10 μl of the attached Pfu buffer. The thus obtained PCR product was double-digested with BamHI and KpnI, the resulting DNA fragment of about 720 bp was integrated into BamBI, KpnI site of the plasmid pM1097 prepared in step (1) and the thus obtained plasmid was named pM1303. This plasmid contains a DNA fragment represented by the nucleotide sequence of SEQ ID NO:14 of the Sequence Listing.

(3) Preparation of Plasmid pM1304

The plasmid pM1303 prepared in the step (2) was double-digested with EcoRI and KpnI, the resulting DNA fragment of about 1150 bp was integrated into EcoRI, KpnI site of a plasmid pM1103 modified by integrating the dhfr gene into pEF-BOS (Mizushima S. and Nagata S., Nucleic Acids Res., vol. 18, p. 5322, 1990), and the thus obtained plasmid was named pM1304. This plasmid is an expression vector of a polypeptide composed of the amino acid sequence of SEQ ID NO:11 of the Sequence Listing (to be referred to as shFas (nd29)-Fc herein in some cases).

(4) Preparation of Plasmid pM1317

Firstly, sense primer 7 (TGCGAATTCACCATGCTGGG CATCTGG) and antisense primer 8 (CGGGGTACCTCAC TATGGGCACGGTGGGCA) were chemically synthesized (SEQ ID NOS:7 and 8 in the Sequence Listing, respectively). This sense primer 7 contains EcoRi site (GGATCC) and 5'-end region of a sequence which encodes the human Fas antigen signal peptide. The antisense primer 8 contains a nucleotide sequence which encodes the C-terminal side amino acids of the hinge region of human immunoglobulin G1 and KpnI site (GGTACC). The PCR reaction was carried our in the same manner as described in the step (1) by preparing 100 μl of a solution which contains 100 pmol of each of the thus obtained sense primer 7 and antisense primer 8, 0.3 μg of the plasmid 1304 prepared in (3), 20 nmol of each of dATP, dCTP, dGTP and dTTP, and 2.5 units of Pfu DNA polymerase and 10 μl of the attached Pfu buffer. The thus obtained PCR product was double-digested with EcoRI and KpnI, the resulting DNA fragment of about 450 bp was integrated into EcoRI, KpnI site of the plasmid pM1103 used in the step (3), and the thus obtained plasmid was named pM1317. This plasrnid is an expression vector of a polypeptide composed of the amino acid sequence of SEQ ID NO:10 of the Sequence Listing (to be referred to as shFas(nd29)-hinge herein in some cases). In this connection, an *E. coil* strain JM109 was transformed with the plasmids pM1304 and pM1317 in the usual way, and the thus obtained transforrnants JM109(pM1304) and JM109(pM1317) have been deposited by the present inventors in National Institute of Bioscience and Human Technology, Higashi-1-1-3, Tsukuba-Shi, Ibaraki, Japan, on Mar. 14, 1996, which have been transferred on Mar. 6, 1997, under the Budapest Treaty (FERN BP-5854 and FERN BP-5855).

Inventive Example 2

Preparation and Culturing of Transformant

Using pM1304, pM1317 and pBF-Fc1 which has been described in Example 1 of International Patent Application WO 95/13293 (an expression plasmid of a chimera protein (to be referred to as hFas-Fc herein in some cases) of the extracellular region of human Fas antigen and Fc region of human IgG1), transformants COS-1/pM1304, COS-1/pM1317 and COS-1/pBF-Fc1 were prepared in the following manner. That is, 100 μg of each plasmid DNA was dissolved in 500 μl of a 10 mM Tris-HCl (pH 7.4)/1 mM ethylenediaminetetraacetic acid solution (to be referred to as TE buffer hereinafter). To each of the resulting solutions was added 125 ml of D-MEM (Nissui Pharmaceutical) containing 0.2 mg/ml of DEAE-dextran and 50 mM Tris-HCl (pH 7.4), thereby obtaining a DNA-DEAE-dextran mixture solution. The DNA-DEAE-dextran mixture solution was added to COS-1 cells which have been monolayer-cultured to their semi-confluent state using a 1,700 $cm^2$ capacity roller bottle (manufactured by Corning), and the cells were cultured at 37° C. to obtain the transformants COS-1/pM1304, COS-1/pM1317 and COS-1/pBF-Fc1. After 4 hours of the culturing, the DNA-DEAE-dextran mixture solution was removed and replaced by D-MEM medium containing 10% fetal calf serum (manufactured by Lifetech Oriental), and the cells were cultured for additional 24 hours. Thereafter, the medium was changed to phenol red free D-MEM (no addition of FBS and BSA), the cells were again cultured for 72 hours and then the culture supernatant was recovered.

Inventive Example 3

Purification of shFas(nd29)-Fc (1) Affinity Chromatography

Ammonium sulfate (mfd. by Wako Pure Chemical Industries) was added to, and dissolved in, one liter of COS-1/pM1304 culture supernatant to 70% saturation, and the solution was allowed to stand overnight at 4° C. The thus formed precipitate was recovered by 30 minutes of centrifugation at 8,000 rpm and at 4° C., suspended in phosphate-buffered saline (PBS) and then dialyzed against PBS. A 57 ml portion of the thus prepared suspension was diluted with two volumes of Affi-prep Protein A Binding Buffer (manufactured by Bio-Rad). After removing the insoluble matter by filtration, the resulting solution was applied to an Affi-prep Protein A Preparative Cartridge (7.3 ml, manufactured by Bio-Rad) column which has been equilibrated in accordance with the instructions. The column was washed with 90 ml of Affi-prep Protein A Binding Buffer and then shFas(nd29)-Fc was eluted with Affi-prep Protein A Elution Buffer (manufactured by Bio-Rad). Fractions containing shFas(nd29)-Fc which was detected by ELISA making use of a monoclonal antibody specific for human Fas antigen were pooled, subjected to ultrafiltration using Filtron Omega Cell (manufactured by Fuji Filter; nominal molecular weight cutoff of 30 kD) and then concentrated. The thus concentrated solution was dialyzed against 0.9% NaCl, thereby obtaining purified shFas(nd29)-Fc. Also, hFas-Fc was purified in the same manner. The protein content of each sample was measured in accordance with the method of Lowry using bovine serum albumin as the standard substance.

(2) SDS-page

The purified shFas(nd29)-Fc obtained in the above step (1) was subjected to polyacrylamide gel electrophoresis using a 5 to 20% gradient gel containing 0.1% SDS, and the band was detected by staining the gel with 2D-Silver Staining Reagent II "Daiichi" (manufactured by Daiichi Pure Chemicals). Results of the purification of shFas(nd29)-Fc are shown in FIG. 6. In the drawing, lanes 1 to 4 show results under a non-reducing condition, and lanes 5 to 8 under a reducing condition. As shown in FIG. 6, the purified shFas (nd29)-Fc was detected as an almost single band corresponding to its dimer having a molecular weight of about 85 kD under the non-reducing condition (lanes 1 to 3) or corresponding to its monomer having a molecular weight of about 43 kD under the reducing condition (lanes 5 to 7).

Inventive Example 4
Analysis of shFas(nd29)-Fc N-terminal Amino Acid Sequence
(1) Desalting of Test Sample by Reverse Phase HPLC The purified shFas(nd29)-Fc obtained in Inventive Example 3 was subjected to a reverse phase HPLC in the following manner. Firstly, the aforementioned purified shFas (nd29)-Fc was applied to a VYDAC C4 column (4.6 mmØ× 25 cm, manufactured by Cypress) which had been equilibrated with 0.05% trifluoroacetic acid in advance, and the column was then washed with 0.05% trifluoroacetic acid. After the washing, elution was carried out by a linear density gradient method at a flow rate of 1 ml/min using 0.05% trifluoroacetic acid/0–100% acetonitrile.

(2) Analysis of N-terminal Amino Acid Sequence

The eluted main peak fraction was lyophilized and dissolved in 70% formic acid, and N-terminal amino acid sequence of the thus prepared sample was determined using Model 477A Protein Sequencing System-120 APTH Analyzer (manufactued by Perkin-Elmer). That is, PTH amino acids were detected at an ultraviolet absorption of 270 nm, and the amino acids were identified based on the retention time of standard PTH amino acids (manufactured by Perkin-Elmer) which have been isolated in advance by the same method. As the results, it was confirmed that the sample has an N-terminal amino acid Bequence (Thr Gln Asn Leu Glu Gly Leu His His Asp (SEQ ID NO:24)) in which 29 amino acid residues are deleted from the N-terminus of human Fas antigen.

Inventive Example 5
Comparison of Apoptosis Inhibition Activities of shFas (nd29)-Fc and hFas-Fc The measurement was carried out based on the activity of shFas(nd29)-Fc and hFas-Fc to inhibit cytotoxic activities of 1A12 cells and FLm14 cells upon WC8 cells and W4 cells. The 1A12 cells are cells obtained by transforming mouse WR19L cells to express human Fas ligand, and the FLm14 cells are cells obtained by transforming mouse FDC-P1 cells to express mouse Fas ligand. The WC8 cells and W4 cells are cells obtained by transforming mouse WR19L cells to express human Fas antigen and mouse Fas antigen, respectively. The WR19L cells are cells which can hardly express mouse Fas antigen and are sensitive to the cytotoxicity of TNF. Measurement of the cytotoxic activity was carried out in accordance with the method of Rouvier E. et al. (*J. Exp. Med.*, vol. 177, pp. 195–200, 1993). Firstly, 1A12 cells or FLm14 cells were washed with RPMI 1640 containing 10% of immobilized FBS and used as the effector cells. On the other hand, $1 \times 10^6$ of WC8 cells or W4 cells were incubated at 37° C. for 2 hours in 100 µl of RPMI 1640 containing 10% of immobilized FBS together with 20 µCi of [$^{51}$Cr] sodium chromate (manufactured by NEN). After washing with RPMI 1640 containing 10% of immobilized FBS, these cells were used as the target cells. Together with varied amounts of shFas(nd29)-Fc and hFas-Fc, $1 \times 10^4$ of 1A12 cells or $1 \times 10^5$ of FLm14 cells were mixed with $1 \times 10^4$ of the target cells in each round bottom well of a microtiter plate. In this case, the total liquid volute was adjusted to 100 µl. The thus prepared plate was centrifuged at 800 rpm for 2 minutes and then incubated at 37° C. for 4 hours. Thereafter, the plate was centrifuged at 1,200 rpm for 5 minutes, and a 50 µl portion of the supernatant was collected from each well to measure the radioactivity using a γ counter, thereby calculating specific cell lysis ratio. Spontaneous release of $^{51}$Cr was determined by incubating the target cells in the medium alone, and its maximum release was determined by adding Triton X-100 to the target cells to a concentration of 0.1%.

The specific cell lysis ratio was calculated by the following formula.

$$\text{Specific cells lysis ratio (\%)} = \frac{\text{observed release of } ^{51}Cr - \text{spontaneous release of } ^{51}Cr}{\text{maximum release of } ^{51}Cr - \text{spontaneous release of } ^{51}Cr} \times 100$$

Figure 9:
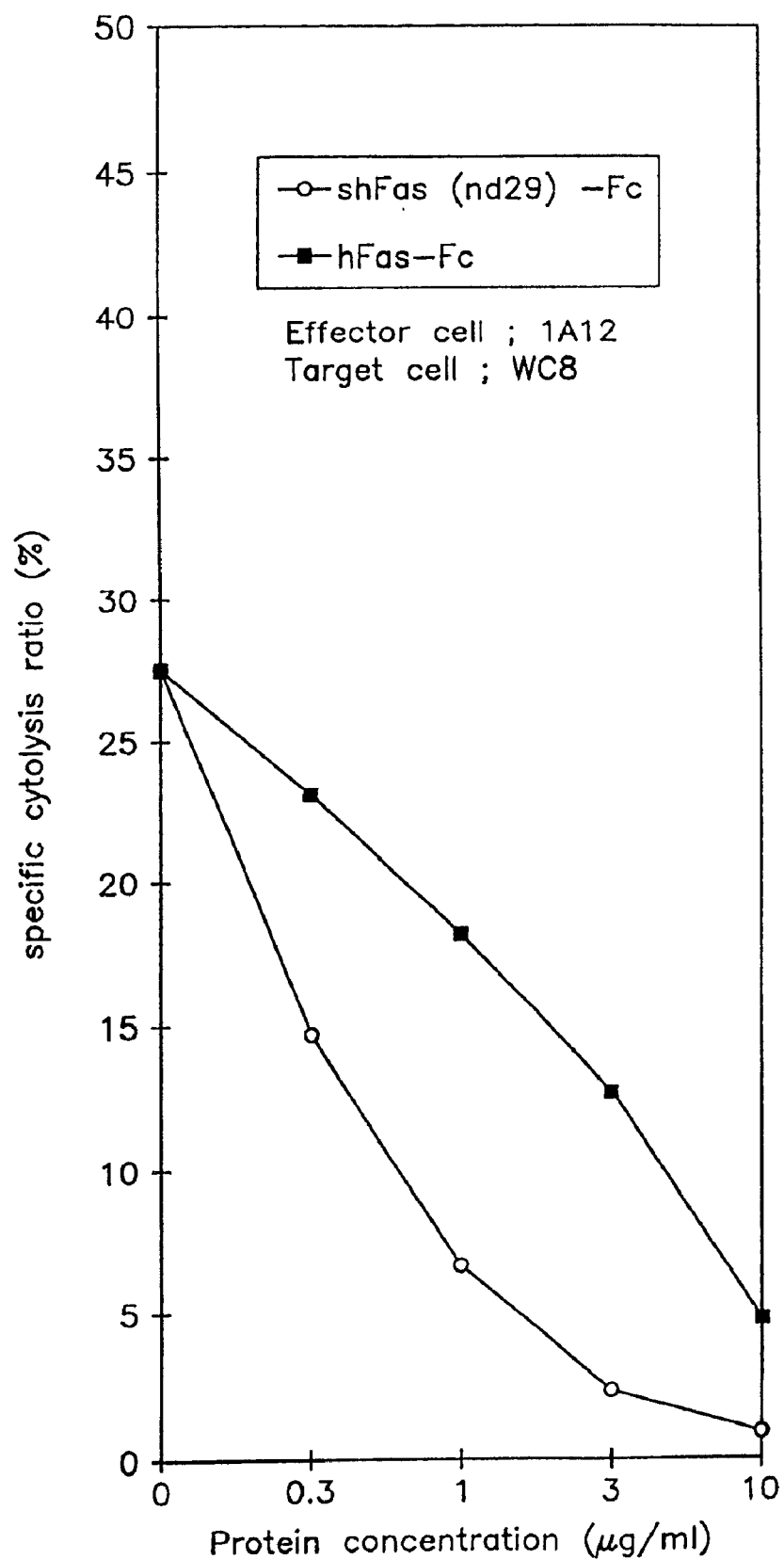
FIG. 9 is a graph showing cell apoptosis inhibiting activity of hFas-Fc and shFas(nd29)-Fc.
Figure 10:
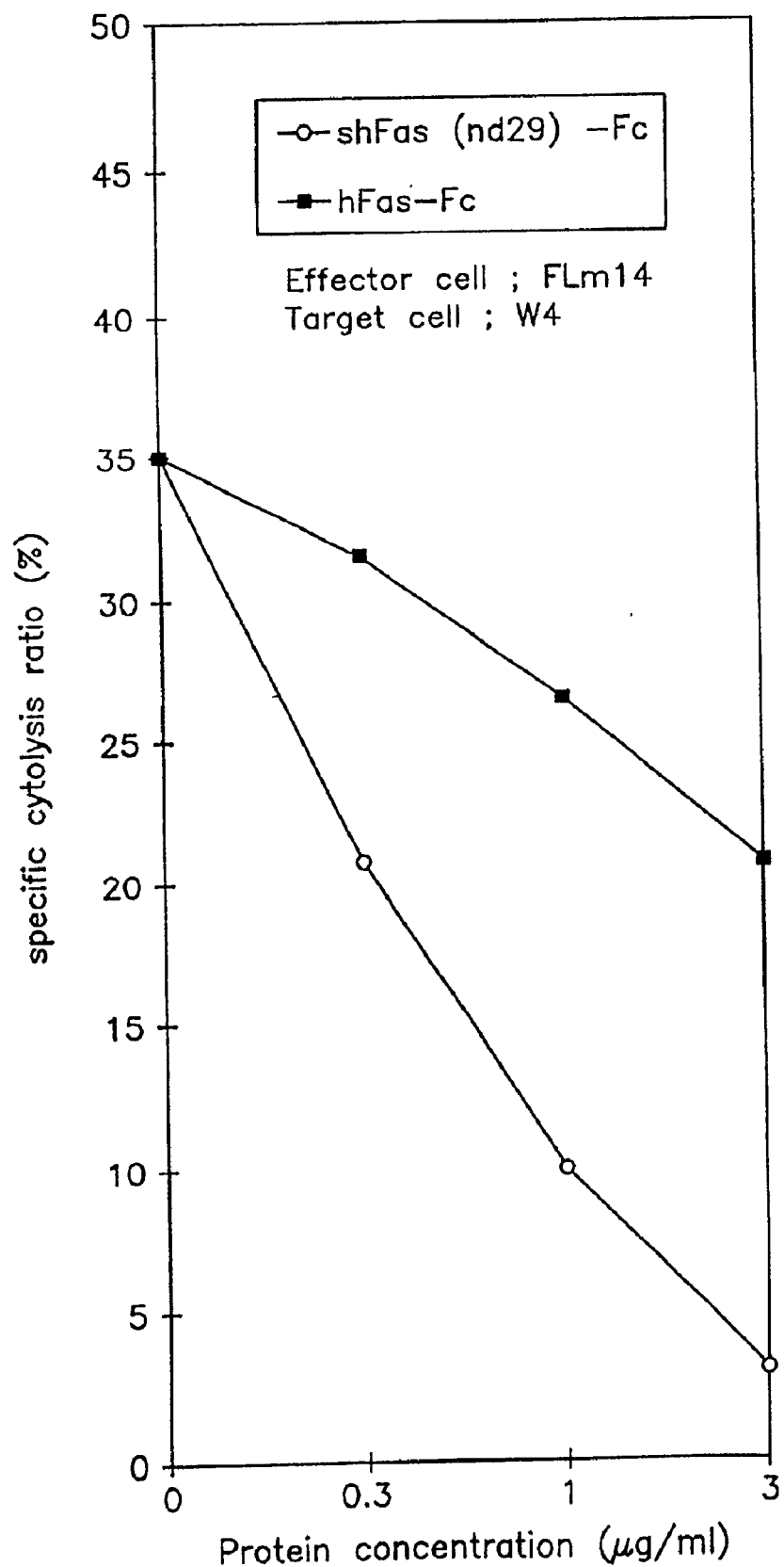
FIG. 10 is a graph showing cell apoptosis inhibiting activity of hFas-Fc and shFas(nd29)-Fc.

FIG. 9 shows specific cytotoxicity inhibition activities of shFas(nd29)-Fc and hFas-Fc when 1A12 cells were used as the effector cells and WC8 cells as the target cells, and FIG. 10 shows specific cytotoxicity inhibition activities of shFas (nd29)-Fc and hFas-Fc when FLm14 cells were used as the effector cells and W4 cells as the target cells. As shown in FIGS. 9 and 10, shFas(nd29)-Fc was possessed of 3 to 10 times higher cytotoxicity inhibition activity than that of Fas-Fc.

Inventive Example 6
Purification of shFas(nd29)-hinge
(1) Preparation of Anti-Fas Antigen Monoclonal Antibody-immobilized Affinity Column A 350 mg portion of an anti-Fas antigen monoclonal antibody (4B4-B3) which has been prepared in accordance with a known method (Kohler and Milstein, *Nature*, vol. 256, p. 495, 1975) using mouse myeloma cells and spleen cells of mouse immunized with human Fas antigen was mixed with 120 ml of Formyl-Cellulofine (manufactured by Seikagaku Kogyo) and stirred at 4° C. for 2 hours. This was then mixed with 650 mg of trimethylamine borane (manufactured by Wako Pure Chemical Industries) and stirred overnight to effect binding of the antibody. In order to remove un-immobilized antibody molecules, the resin was washed with 2.4 liters of ultra-pure water. Thereafter, this was stirred at 4° C. for 3 hours in 0.2 M Tris-HCl (pH 8.0) together with 650 mg of trimetylamine borane to block unreacted formyl group, thereby obtaining the antibody affinity column.

(2) Affinity Chromatography

A ten liter portion of COS-1/pM1317 culture supernatant was concentrated to 1.5 liters by ultrafiltration using Filtron Mini Set (manufactured by Fuji filter; 10 kD in nominal molecular weight cutoff). Thereafter, the concentrate was adjusted to pH 8.0 by adding 1 M Tris-HCl (pH 9.0) and applied to the anti-Fas antigen monoclonal antibody-immobilized affinity column which has been equilibrated in advance with 50 mM Tris-HCl 320 ml of (pH 8.0) containing 1 M NaCl. After washing the column with 50 mM Tris-HCl (pH 8.0) containing 1 M NaCl, shFas(nd29)-hinge was eluted with 0.1 M glycine-HCl (pH 2.5) containing 1 M NaCl. Fractions containing shFas(nd29)-hinge detected by ELISA were pooled, subjected to ultrafiltration using Filtron Omega Cell (manufactured by Fuji filter; 10 kD in nominal molecular weight cutoff) and then concentrated. By dialyzing the concentrate against 0.9% NaCl, purified shFas (nd29)-hinge was obtained.

(3) SDS-page

Figure 7:
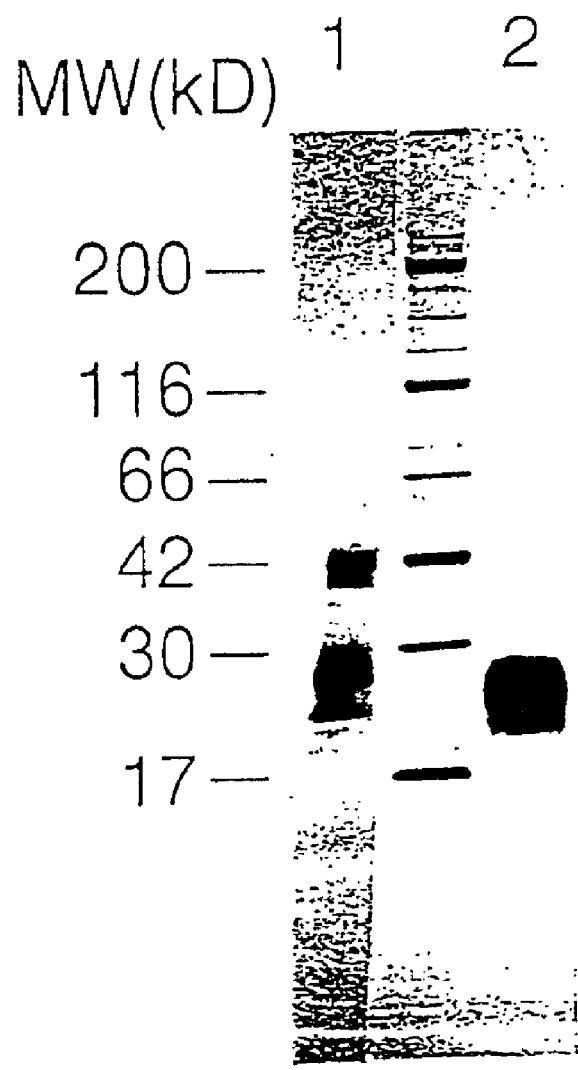
FIG. 7 is a photograph showing results of gel electrophoresis of shFas(nd29)-hinge before gel filtration chromatography.

The purified shFas(nd29)-hinge obtained in the above step (2) was subjected to polyacrylamide gel electrophoresis using a 5 to 20% gradient gel containing 0.1% SDS, and the band was detected by staining the gel with 2D-Silver Staining Reagent II "Daiichi" (manufactured by Daiichi Pure Chemicals). Results of the purification of shFas(nd29)-hinge are shown in FIG. 7. In the drawing, lane 1 shows results under a non-reducing condition, and lane 2 under a reducing condition. As shown in FIG. 7, the purified shFas(nd29)-hinge was detected as two bands having molecular weights of about 43 kD and about 27 kD under the non-reducing condition or as two bands having molecular weights of about 23 kD and 27 kD under the reducing condition.

(4) Gel Filtration Chromatography

Figure 8:
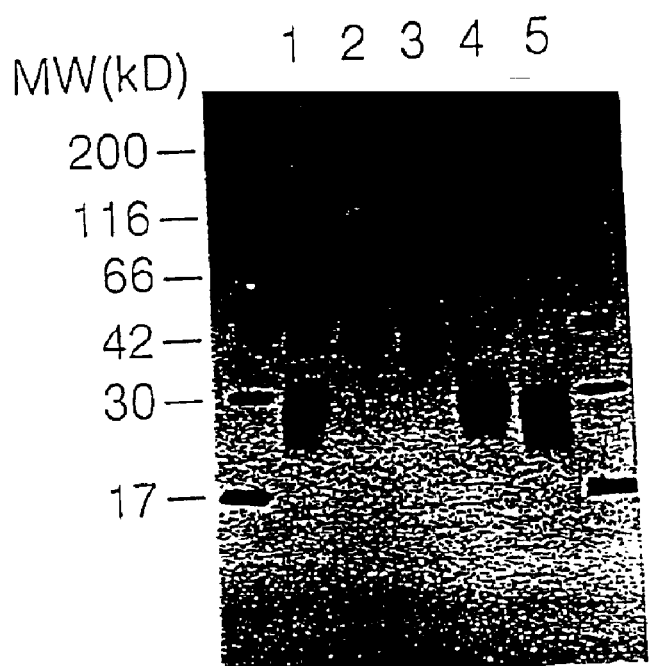
FIG. 8 is a photograph showing results of gel electrophoresis of shFas(nd29)-hinge after gel filtration chromatography.

Gel filtration of the shFas(nd29)-hinge obtained in Inventive Example 6 (2) was carried out by applying it to Sephadex 75 column (manufactured by Pharmacia) which has been equilibrated in advance with 50 mM Tris-HCl/0.5 M NaCl (pH 8.0) and then eluting it with 50 mM Tris-HCl/ 0.5 M NaCl (pH 8.0), and the fractionation was effected using absorbance at 214 nm as the indicator. In the same manner as described in Inventive Example 6 (2), each fraction was concentrated and subjected to polyacrylamide gel electrophoresis. As shown in FIG. 8, it was able to separate a band which was contained in the higher molecular weight fraction (fractions 1 and 2) and seemed to be corresponding to a dimer from another band which was contained in the lower molecular weight fraction (fractions 3 and 4) and seemed to be corresponding to a monomer. Though both fractions showed the cytotoxicity inhibition activity by the assay described in Inventive Example 8, the high molecular weight side fraction showed more stronger activity (about 50 times or more).

Inventive Example 7

Analysis of shFas(nd29)-hinge N-terminal Amino Acid Sequence

Using the purified shFas(nd29)-hinge obtained in Inventive Example 6 (2), its N-terminal amino acid sequence was determined using Model 477A Protein Sequencing System-120 APTH Analyzer (manufactured by Perkin-Elmer). That is, PTH amino acids were detected at an ultraviolet absorption of 270 nm, and the amino acids were identified based on the retention time of standard PTH amino acids (manufactured by Perkin-Elmer) which have been isolated in advance by the same method. As the results, it was confirmed that the sample has an N-terminal amino acid sequence in which 29 amino acid residues are deleted from the N-terminus of human Fas antigen.

Inventive Example 8

Comparison of Apoptosis Inhibition Activities of shFas (nd29)-hinge and hFas-Fc

Figure 11:
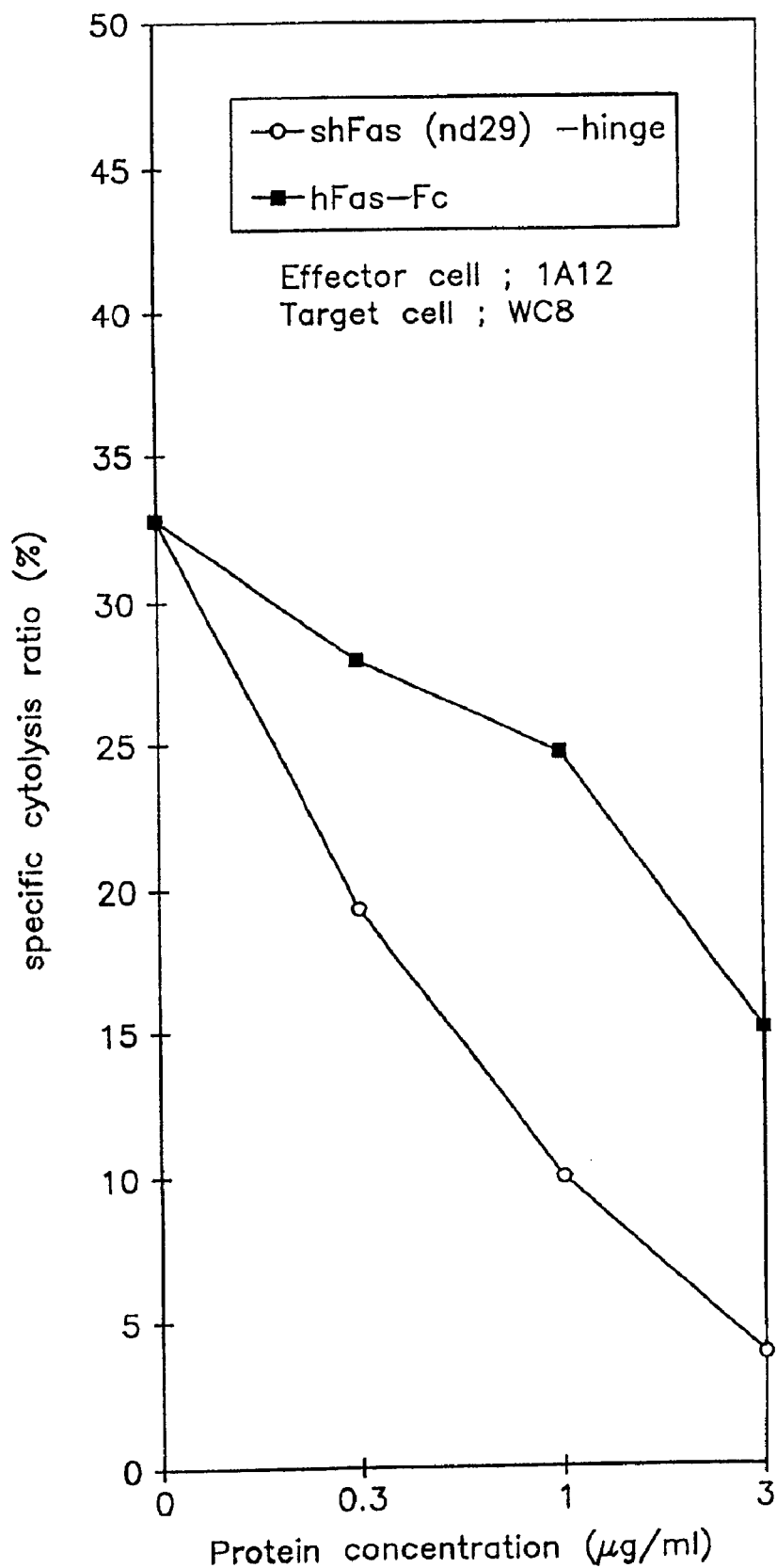
FIG. 11 is a graph showing cell apoptosis inhibiting activity of hFas-Fc and shFas(nd29)-hinge.
Figure 13A:
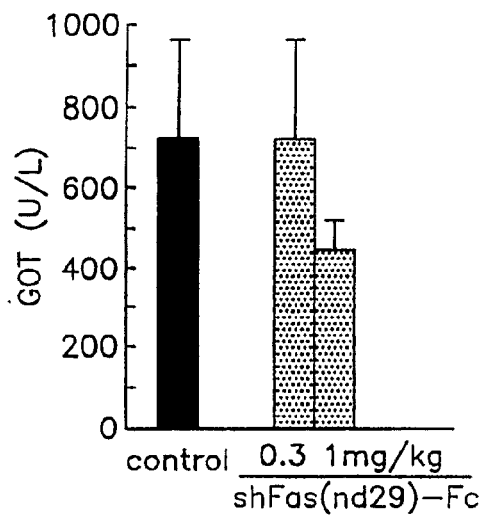
FIGS. 13(*a*) to (*d*) are graphs showing activities of hFas-Fc and shFas(nd29)-Fc to inhibit increment of GOT and GPT.
Figure 13B:
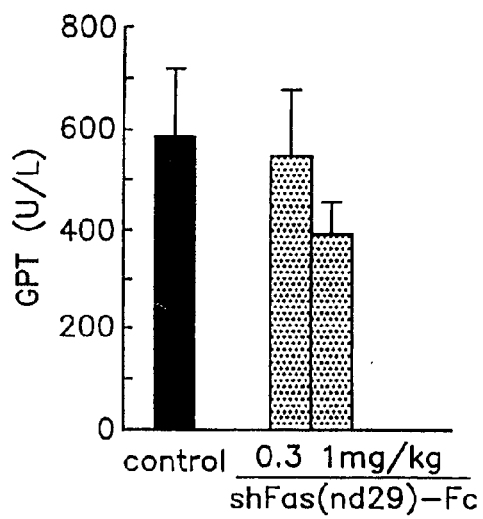
Figure 13C:
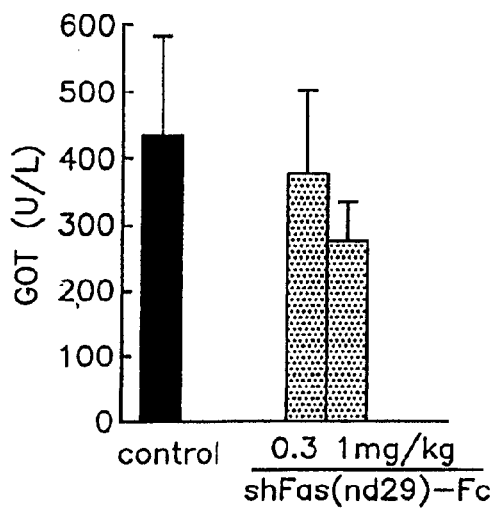
Figure 13D:
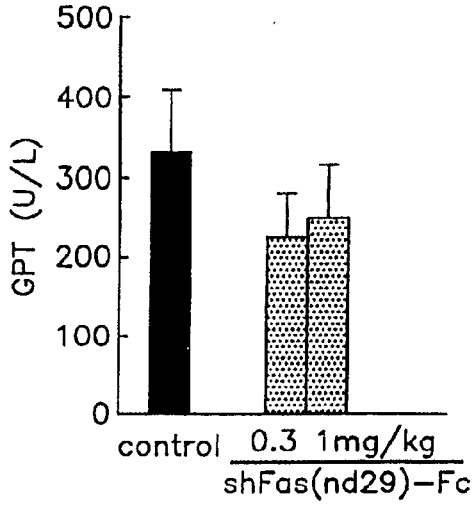
Figure 14A:
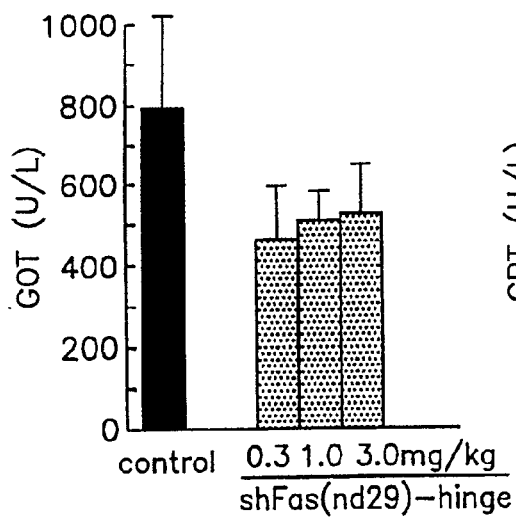
FIGS. 14(*a*) to (*d*) are graphs showing actions of hFas-Fc and shFas(nd29)-hinge to inhibit increment of GOT and GPT.
Figure 14B:
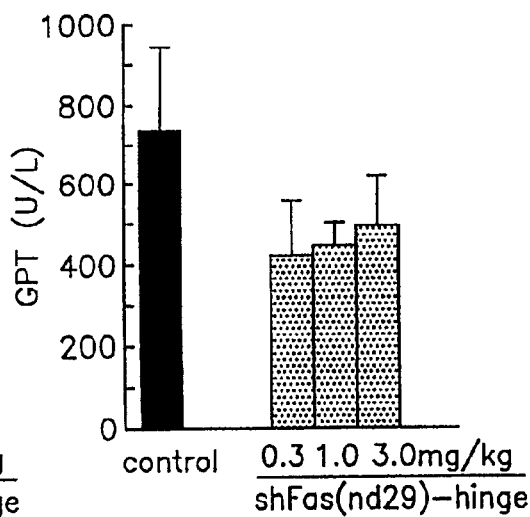
Figure 14C:
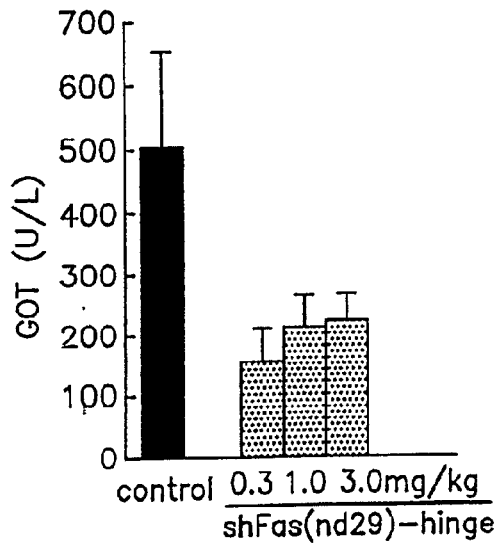
Figure 14D:
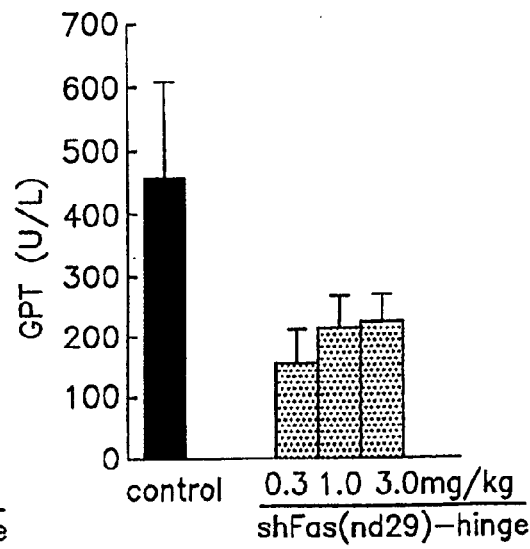

The activity of shFas(nd29)-hinge and hFas-Fc to inhibit cytotoxic activities of 1A12 cells and FLm14 cells upon WC8 cells and W4 cells was measured in the same manner as described in Inventive Example 5. Specific cytotoxicity inhibition activities of shFas(nd29)-hinge and hFas-Fc when 1A12 cells were used as the effector cells and WC8 cells as the target cells are shown in FIG. 11, and specific cytotoxicity inhibition activities of shFas(nd29)-hinge and hFas-Fc when FLm14 cells were used as the effector cells and W4 cells as the target cells are shown in FIG. 12. As shown in FIGS. 11 and 12, shFas(nd29)-hinge was possessed of 3 to 10 times higher cytotoxicity inhibition activity than that of Fas-Fc.

Inventive Example 9

Analysis of the Structure in and Around N-terminal Region of the Fas Antigen Extracellular Region By constructing a steric structure model of the Fas antigen extracellular region, an analysis was made on the relationship between the deletion of amino acid residues in the N-terminal region and the Fas antigen-Fas ligand binding. Proteins having known steric structures and high homology with the amino acid sequence of the Fas antigen extracellular region were retrieved from the PROTEIN DATA BANK (PDB) which is a data base of biological high polymer three-dimensional structures, by the FASTA program in the Homology module manufactured by BIOSYM. As the results, it was found that the extracellular region of TNF receptor p55 (PDB-ID ITNR) has high homology in overall structure. Since this structure was in the form of a complex with TNF-$\beta$, it was most suitable also as a reference protein in constructing a model structure of Fas antigen-Fas ligand complex. Also, the TNF-$\alpha$ (PDB-ID INTF) structure was used as a reference protein in the Fas ligand structure. Construction of the model structure was carried out by a homology modeling method using the Homology module manufactured by BIOSYM. The thus constructed initial structure model was subjected to an energy optimization computing (MM computing) using a molecular force field computing software, DISCOVERY, manufactured by BIO-SYM to obtain a Fas antigen-Fas ligand complex model structure. Next, since a part of the N-terminal region of the thus obtained structure could not be generated from the coordinates of the reference protein, structural prediction of this part was carried out. A Fas antigen extracellular region monomer model structure was extracted from the complex structure, and the deleting 31 amino acid residues were automatically added to its N-terminus by the BIOPOLY-MER module manufactured by BIOSYM to minimize the structure. Next, molecular dynamics computing (MD computing) of 1,000 K and 100 pico-seconds was carried out in vacuo, and structures for every 10 pico-seconds were sampled. Each of the thus sampled structures was minimized to be used as the final Fas antigen extracellular region monomer model structure. When these structures were again made into its complex with the Fas ligand model structure, it was predicted that the N-terminal structure of the Fas antigen extracellular region could cause steric hindrance for its binding with the Fas ligand. On the other hand, when the nd29 model structure was subjected to a simulation analysis by MD computing, it was predicted that it could bind to Fas ligand more quickly, because greater part of the structure hindering its binding with Fas ligand was found to be deleted. In addition, an analysis was made on the state of steric hindrance in complex models of a plurality of conformations of the sampled structure with the Fas ligand structure. As the results, it was predicted that, within the range of from the 1st position arginine residue to the 31st position glutamine residue counting from the N-terminus of Fas antigen, degree of the steric hindrance would be reduced with the deletion of more amino acid residues, and apoptosis inhibition activity of the extracellular region of Fas antigen would increase when particularly 13 or 18 or more amino acid residues were deleted. It was predicted also that increase in the activity could hardly be expected by a deletion within the range of from the 36th position leucine residue to the 42nd position phenylalanine residue counting from the N-terminus, and deletion of the 43rd position cysteine residue counting from the N-terminus of Fas antigen would result in the loss of apoptosis inhibition activity due to destruction of the secondary structure formed by the antigen. The three-dimensional structure analysis carried out this time showed that the affinity for Fas ligand can be controlled by cutting N-terminal structure of the Fas antigen extracellular region.

Inventive Example 10

Mouse Hepatopathy Inhibition by shFas(nd29)-Fc

C57BL/6Cr S1c mice (males, 9 weeks of age, purchased from Japan S L C) were divided into 3 groups, 5 animals per group, and used as the animals to be tested. Cells of *Propionibacterium acnes* killed with heat (manufactured by RIBI Immunochemical Corp.) were dissolved in physiological saline (manufactured by Otsuka Pharmaceutical) to a concentration of 1.5 mg/ml, and a 0.2 ml portion of the resulting solution was administered to each of the mice via tail vein. After 8 days of the administration, the shFas (nd29)-Fc prepared in Inventive Example 3 was diluted with a diluent solution (physiological saline containing 0.1% human serum albumin (The Chemo-Sero-Therapeutic Research Institute)) and administered via tail vein in a dosage of 0.3 mg/8 ml/kg or 1 mg/8 ml/kg. The diluent solution alone was administered to the control group. Five minutes thereafter, 0.2 ml of a lipopolysaccharide (manufactured by Sigma) solution prepared by adjusting to a concentration of 5 µg/ml with physiological saline was administered intraperitoneally. After 8 or 24 hours of the lipopolysaccharide administration, 75 µl of blood was collected from, the fundus oculi vein. The thus collected blood was mixed with 8.3 µl of 3.8% sodium citrate (manufactured by Wako Pure Chemical Industries) aqueous solution and centrifuged at 3,000 rpm for 10 minutes. After the centrifugation, the thus obtained blood plasma was frozen with liquid nitrogen and stored at −30° C. until its use. Measurement of GOT and GPT were carried out using GOT-FA Test Wako (manufactured by Wako Pure Chemical Industries), GPT-FA Test Wako (manufactured by Wako Pure Chemical Industries) and an automatic analyzer (Cobasfara, manufactured by Roche). As the results, the GOT and GPT values in a test group in which 1 mg/8 ml/kg of shFas(nd29)-Fc was administered were lower than those of the control group, thus confirming its hepatopathy inhibition effect (FIG. 13).

Inventive Example 11

Mouse Hepatopathy Inhibition Action of shFas(nd29)-hinge

C57BL/6Cr S1c mice (males, 9 weeks of age, purchased from Japan SLC) were divided into 4 groups, 5 animals per group, and used as the animals to be tested. Cells of *Propionibacterium acnes* killed with heat (manufactured by RIBI Immunochemical Corp.) were dissolved in physiological saline (manufactured by Otsuka Pharmaceutical) to a concentration of 1.5 mg/ml, and a 0.2 ml portion of the resulting solution was administered to each of the mice via tail vein. After 8 days of the administration, the shFas (nd29)-hinge prepared in Inventive Example 6 was diluted with a diluent solution (physiological saline containing 0.1% human serum albumin (The Chemo-Sero-Therapeutic Research Institute)) and administered via tail vein in a dosage of 0.3 mg/8 ml/kg, 1 mg/8 ml/kg or 3 mg/8 ml/kg. The diluent solution alone was administered to the control group. Five minutes thereafter, 0.2 ml of a lipopolysaccharide (manufactured by Sigma) solution prepared by adjusting to a concentration of 5 µg/ml with physiological saline was administered intraperitoneally. After 8 or 24 hours of the lipopolysaccharide administration, 75 µl of blood was collected from the fundus oculi vein. The thus collected blood was mixed with 8.3 µl of 3.8% sodium citrate (manufactured by Wako Pure Chemical Industries) aqueous solution and centrifuged at 3,000 rpm for 10 minutes. After the centrifugation, the thus obtained blood plasma was frozen with liquid nitrogen and stored at −30° C. until its use. Measurement of GOT and GPT were carried out using GOT-FA Test Wako (manufactured by Wako Pure Chemical Industries), GPT-FA Test Wako (manufactured by Wako Pure Chemical Industries) and an automatic analyzer (Cobasfara, manufactured by Roche). As the results, the GOT and GPT values in the shFas(nd29)-hinge-administered groups were lower than those of the control group, thus confirming its hepatopathy inhibition effect (FIG. 14).

INDUSTRIAL APPLICABILITY

Since the novel polypeptide (novel Fas antigen derivative) of the present invention can inhibit induction of apoptosis by competitively inhibiting binding of a Fas ligand with a Fas antigen, it can be used for the prevention and treatment of various diseases in which the participation of apoptosis mediated by the Fas antigen is indicated, by controlling the apoptosis mediated by the Fas antigen, particularly an apoptosis generated in the living body caused by an endogenous or exogenous Fas ligand. For example, in the case of certain autoimmune diseases, it will become possible to prevent destruction of organs by inhibiting rapid cell death caused by the attack of autoantigen reactive T cells, through the artificial inhibition of apoptosis making use of the novel Fas antigen derivative. Illustrative examples of such diseases include graft versus host disease (GVHD) and diabetes. It is known that not only infected cells but also un-infected cells are removed by immune reactions when infected with viruses. For example, it is considered that decrease in the immunological capacity at the latter stage of AIDS virus infection and reduction of liver functions by hepatitis, particularly fulminant hepatitis, are results of extreme reduction of tissue functions caused by the apoptosis of immunocytes or hepatocytes. In the case of such conditions, the novel Fas antigen derivative capable of inhibiting apoptosis can be used for the treatment of apoptosis-related infectious diseases caused by viruses, such as influenza, AIDS, hepatitis and the like, and complications thereof. In addition, since Fas antigen seems to be related to the cell death in various organs because of its broad distribution in organs, it may also be useful for the treatment of myocardiopathy in myocardial infarction and the like ischemic heart diseases, such as reperfusion injury, nephritis and multiple organ failure and for the preservation organs at the time of organ transplantation. Particularly, since the novel Fas antigen derivative of the present invention can strongly inhibit apoptosis with a low dosage, it will also be effective in the living body with a low dosage and with less side effects, so that it has high availability from the viewpoint of efficacy, safety and cost. The novel Fas antigen derivative of the present invention which comprises a sequence of human origin is particularly desirable in applying it to human.

Also, the novel Fas antigen derivative which can induce apoptosis when appropriately incorporated into cells is effective in accelerating apoptosis by properly incorporating it into cells in the liposomes or the like form or by properly expressing it on cells by means of gene therapy for example using the DNA of the second aspect of the present invention. In consequence, it is effective in removing unnecessary cells such as virus-infected cells in the early stage of viral infection and also can be used for the prevention and treatment of diseases which seem to be caused by a failure in apoptosis, such as articular rheumatism, SLE and the like.

Also, since it keeps at least a part of the antigenicity of Fas antigen, it can be linked to an anti-Fas antigen antibody, so that it is effective in inhibiting apoptosis caused by the anti-Fas antigen antibody.

Also, since the novel Fas antigen derivative of the present invention binds to Fas ligand with more specific and high affinity, it can be applied to the detection of Fas ligand in human body fluids. Since it can be used for the detection of increment, reduction or abnormality of Fas ligand in various diseases in which the participation of Fas ligand is indicated, it can be applied to the precognition, detection and diagnosis of specific diseases and morbid states and to the selection of therapeutic methods thereof. It is also useful in monitoring patients undergoing medical treatment with Fas ligand, Fas ligand-related substances or drugs which exert influences upon the expression of Fas ligand, and in judging therapeutic effects and prognosis.

On the other hand, the DNA of the second aspect of the present invention and the like are useful for the large scale industrial production of the novel Fas antigen derivative with high purity. Because of this, the novel Fas antigen derivative can be supplied to the field of medicaments as a principal component of therapeutic drugs and also can be applied to diagnostic drugs. In addition, the nucleotide sequence which encodes the novel Fas antigen derivative can be applied to gene therapy and the like.

What is claimed is:

1. An isolated DNA encoding a Fas antigen extracellular region polypeptide, which is SEQ ID No:15, wherein at least one amino acid residue is deleted from the 1st to 42nd amino acid residues counting from the N-terminus of SEQ ID No:15.

2. An isolated DNA encoding a fusion polypeptide consisting of a Fas antigen extracellular region polypeptide, which is SEQ ID No:15, wherein at least one amino acid residue is deleted from the $1^{st}$ to $42^{nd}$ amino acid residues counting from the N-terminus of SEQ ID No: 15; and a peptide or a polypeptide, which is polymerizable.

3. An isolated DNA encoding a fusion polypeptide consisting of a Fas antigen extracellular region polypeptide, which is SEQ ID No:15, wherein at least one amino acid residue is deleted from the $1^{st}$ to $42^{nd}$ amino acid residues counting from the N-terminus of SEQ ID NO:15; and at least one peptide or polypeptide of immunoglobulin selected from the group consisting of the hinge region, the CH2 region, the CH3 region and CH4 region.

4. An isolated DNA according to claim 1 wherein said number of deleted amino acid residues in said Fas antigen extracellular region polypeptide is from 29 to 42.

5. An isolated DNA encoding a fusion polypeptide consisting of a Fas antigen extracellular polypeptide, which is SEQ ID No:15, wherein 29 to 42 amino acid residues are deleted from the 1st to 42nd amino acid residues counting from the N-terminus of SEQ ID No: 15; and a peptide or a polypeptide, which is polymerizable.

6. An isolated DNA encoding a Fas antigen extracellular polypeptide, which is SEQ ID No:15, wherein from 29 to 42 amino acid residues are deleted from the $1^{st}$ to $42^{nd}$ amino acid residues counting from the N-terminus of the SEQ ID NO: 15; and at least one peptide or polypeptide of imrnunoglobulin selected from the group consisting of the hinge region, the CH2 region, the CH3 region and CH4 region.

7. An isolated DNA according to claim 1 wherein said polypeptide further consists of at least one polypeptide selected from the group consisting of Fas antigen transmembrane region polypeptide and Fas antigen cytoplasrnic tail region polypeptide.

8. An isolated DNA encoding a fusion polypeptide consisting of a Fas antigen extracellular region polypeptide, which is SEQ ID No:15, wherein at least one amino acid residue is deleted from the 1st to 42nd amino acid residues counting from the N-terminus of SEQ ID No: 15; at least one polypeptide selected from the group consisting of Fas antigen transmembrane region polypeptide and Fas antigen cytoplasmic tail region polypeptide; and a peptide or a polypeptide, which is polymerizable.

9. An isolated DNA encoding a fusion polypeptide consisting of a Fas antigen extracellular region polypeptide, which is SEQ ID No:15, wherein at least one amino acid residue is deleted from the $1^{st}$ to $42^{nd}$ amino acid residues counting from the N-terminus of SEQ ID NO: 15; at least one polypeptide selected from the group consisting of Fas antigen transmembrane region polypeptide and Fas antigen cytoplasmic tail region polypeptide; and at least one peptide or polypeptide of immunoglobulin selected from the group consisting of the hinge region, the CH2 region, the CH3 region and CH4 region.

10. An isolated DNA according to claim 1 wherein said polypeptide further comprises at least one amino acid mutation with the proviso said Fas antigen extracellular region polypeptide retains its activity of inhibiting apoptosis.

11. An isolated DNA according to claim 1 wherein said polypeptide further comprises at least one amino acid mutation with the proviso said Fas antigen extracellular region polypeptide retains its activity of inhibiting apoptosis.

12. An isolated DNA encoding a fusion polypeptide consisting of a Fas antigen extracellular region polypeptide, which is SEQ ID No:15, wherein at least one amino acid residue is deleted from the $1^{st}$ to $42^{nd}$ amino acid residues counting from the N-terminus of SEQ ED NO: 15, wherein said polypeptide further comprises at least one amino acid mutation with the proviso said Fas antigen extracellular region polypeptide retains its activity of inhibiting apoptosis; and at least one peptide or polypeptide of immunoglobulin selected from the group consisting of the hinge region1 the CH2 region, the CH3 region and CH4 region.

13. A recombinant DNA molecule which consists of the DNA of claim 1.

14. An expression vector containing the DNA of claim 1.

15. A host cell containing the vector of claim 14.

16. A method for producing the polypeptide encoded by the DNA of claim 1, which comprises the steps of culturing a host cell containing an expression vector containing said and at least one step selected from the group consisting of recovering and purifying the polypeptide from a culture mixture.

17. A recombinant DNA molecule which consists of the DNA of claim 2.

18. An expression vector containing the DNA of claim 2.

19. A host cell containing the vector of claim 2.

20. A method for producing the fusion polypeptide encoded by the DNA of claim 2, which comprises the steps of culturing a host cell containing an expression vector containing said DNA and at least one step selected from the group consisting of recovering and purifying the fusion polypeptide from a culture mixture.

* * * * *